US011234792B2

(12) United States Patent
Yamamoto et al.

(10) Patent No.: US 11,234,792 B2
(45) Date of Patent: Feb. 1, 2022

(54) METHOD OF ESTIMATING AND RESTORING ABUTMENT TOOTH FORM CHANGED BY SCANNING AND PROGRAM THEREOF

(71) Applicant: KABUSHIKI KAISHA SHOFU, Kyoto (JP)

(72) Inventors: Makoto Yamamoto, Osaka (JP); Ryohei Kondo, Kyoto (JP); Tomoyuki Inoue, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 604 days.

(21) Appl. No.: 16/156,285

(22) Filed: Oct. 10, 2018

(65) Prior Publication Data
US 2019/0125490 A1    May 2, 2019

(30) Foreign Application Priority Data

Oct. 31, 2017   (JP) .............................. JP2017-211062

(51) Int. Cl.
*A61C 5/77*     (2017.01)
*A61C 13/00*    (2006.01)
(Continued)

(52) U.S. Cl.
CPC .............. *A61C 5/77* (2017.02); *A61C 9/0046* (2013.01); *A61C 9/0053* (2013.01);
(Continued)

(58) Field of Classification Search
CPC ......... G06T 7/62; G06T 7/0012; G06T 15/08; G06T 17/10; G06T 19/20;
(Continued)

(56) References Cited

U.S. PATENT DOCUMENTS 5,417,572 A *   5/1995   Kawai ................ A61C 13/0004
                                                 433/218
7,112,065 B2 *  9/2006   Kopelman ......... A61C 13/0004
                                                 433/213
(Continued)

FOREIGN PATENT DOCUMENTS

JP       2011-143181      7/2011
JP       2013-169239      9/2013
(Continued)

OTHER PUBLICATIONS

Persson, Anna, et al. "A three-dimensional evaluation of a laser scanner and a touch-probe scanner." The Journal of prosthetic dentistry 95.3 (2006): 194-200.*
(Continued)

*Primary Examiner* — David T Welch
(74) *Attorney, Agent, or Firm* — Wenderoth, Lind & Ponack, L.L.P.

(57) ABSTRACT

A method of estimating and restoring includes: determining a temporary finish line having multiple points on scan data as an imaginary boundary line between a formed portion and an unformed portion of the abutment tooth or abutment tooth model; deleting the scan data including the temporary finish line in an edge portion of the abutment tooth or abutment tooth model; extending, in a portion in which the scanned data is deleted, a crown-side temporary finish line and a root-side temporary finish line in directions supplementing the deleted portion of the scan data, respectively; and estimating and restoring the finish line of the edge portion which is formed on the outer side than the edge portion of the deleted scan data based on the extended crown-side temporary finish line and the extended root-side temporary finish line.

20 Claims, 13 Drawing Sheets

(51) Int. Cl.
*A61C 9/00* (2006.01)
*G16H 50/50* (2018.01)
*G06F 30/00* (2020.01)
*G06F 30/10* (2020.01)
*G06T 19/20* (2011.01)
*G06T 7/00* (2017.01)
*G06T 7/62* (2017.01)
*G06T 17/10* (2006.01)
*G06T 15/08* (2011.01)

(52) U.S. Cl.
CPC .......... *A61C 13/0004* (2013.01); *G06F 30/00* (2020.01); *G06F 30/10* (2020.01); *G06T 7/0012* (2013.01); *G06T 7/62* (2017.01); *G06T 15/08* (2013.01); *G06T 17/10* (2013.01); *G06T 19/20* (2013.01); *G16H 50/50* (2018.01); *G06T 2207/30036* (2013.01); *G06T 2210/41* (2013.01); *G06T 2219/2021* (2013.01)

(58) Field of Classification Search
CPC ....... G06T 2207/30036; G06T 2210/41; G06T 2219/2021; G06F 30/10; A61C 13/0004
See application file for complete search history.

(56) References Cited

U.S. PATENT DOCUMENTS

| | | | | |
|---|---|---|---|---|
| 7,974,721 | B2* | 7/2011 | Shibata | A61C 5/77 700/98 |
| 2004/0220691 | A1* | 11/2004 | Hofmeister | A61C 13/0004 700/98 |
| 2006/0115793 | A1* | 6/2006 | Kopelman | A61B 5/0002 433/215 |
| 2013/0110469 | A1* | 5/2013 | Kopelman | A61C 13/0004 703/1 |
| 2016/0135931 | A1* | 5/2016 | Morales | A61C 8/0089 433/213 |
| 2016/0256035 | A1* | 9/2016 | Kopelman | A61C 9/0053 |
| 2019/0209274 | A1* | 7/2019 | Barak | A61C 1/084 |

FOREIGN PATENT DOCUMENTS

| | | |
|---|---|---|
| WO | 2008/066891 | 6/2008 |
| WO | 2012/055420 | 5/2012 |
| WO | 2016/046308 | 3/2016 |

OTHER PUBLICATIONS

Hollenbeck, Karl, Thomas Allin, and Mike van der Poel. "Dental Lab 3D Scanners—How they work and what works best." Copenhagen: 3Shape Technology Research (2012): 1-5.*

Extended European Search Report dated Feb. 20, 2019 in corresponding European Patent Application No. 18200313.7.

Yamamoto Precious Metal Co., Ltd., Dental CAD/CAM Handbook II, Nov. 16, 2015 (with partial English translation).

Notice of Reasons for Refusal dated Oct. 12, 2021 in corresponding Japanese Patent Application No. 2017-211062, with English Machine Translation.

* cited by examiner

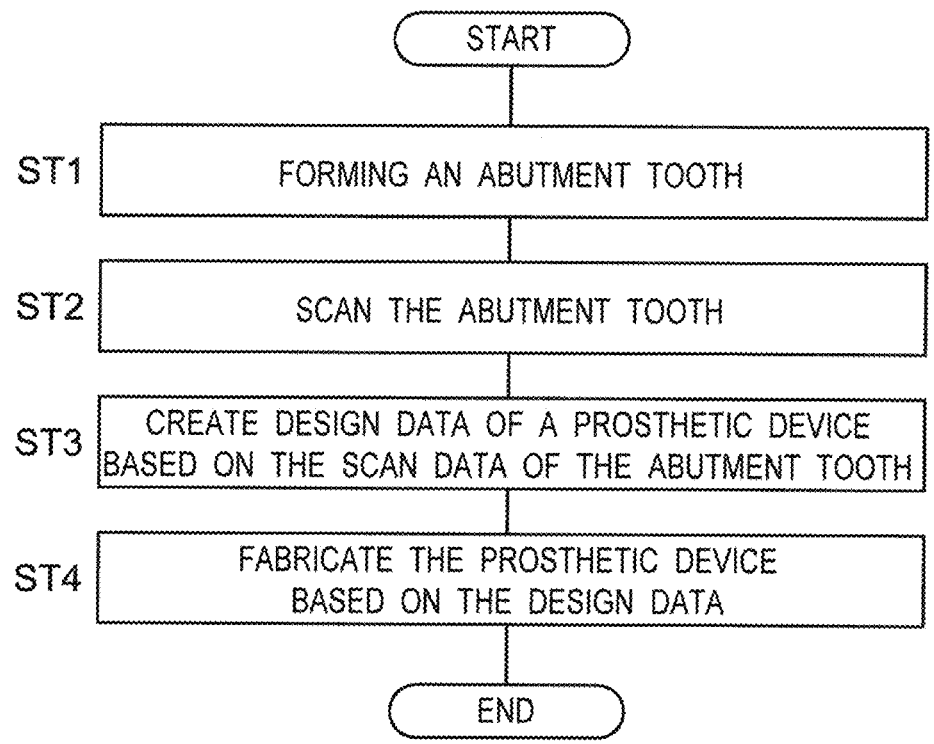
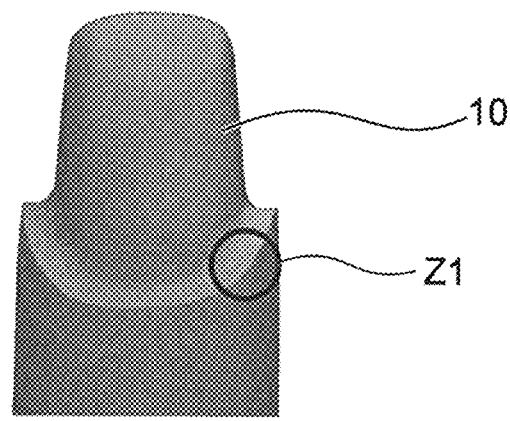

METHOD OF ESTIMATING AND RESTORING ABUTMENT TOOTH FORM CHANGED BY SCANNING AND PROGRAM THEREOF

TECHNICAL FIELD

The present invention relates to a method of estimating and restoring an abutment tooth or an abutment tooth form near a finish line changed by scanning and a program thereof. Particularly, the present invention relates to a portion of a manufacturing process of a prosthetic device to which a digital dental instrument is applied in dentistry, i.e., a method and a program of estimating and restoring a shape near a finish line originally possessed by an abutment tooth or an abutment tooth model and the finish line from scan data acquired by scanning the abutment tooth or abutment tooth model with an intraoral scanner or a desktop scanner.

BACKGROUND ART

Recently, in production of a prosthetic device to which a digital dental instrument is applied in dentistry, an abutment tooth or abutment tooth model is scanned to reproduce an abutment tooth or an abutment tooth form, so as to fabricate a prosthetic device fitting to an originally-possessed abutment tooth form.

For example, Patent Document 1 discloses a device using tooth profile data acquired by scanning a tooth profile model of a registrant to extract a shape of a tooth corresponding to a lost tooth from tooth row data as prosthesis data of a dental prosthesis.

Non-Patent Document 1 discloses as prosthesis production using dental CAD/CAM a procedure of fabricating a prosthesis based on data acquired by scanning an abutment tooth or abutment tooth model.

CITATION LIST

Patent Literature

Patent Document 1: Japanese Laid-Open Patent Publication No. 2013-169239

Non Patent Literature

Non-Patent Document 1: Yamamoto Precious Metal Co., Ltd., "Dental CAD/CAM Handbook II", Nov. 16, 2015

SUMMARY OF INVENTION

Technical Problem

However, scanning of an abutment tooth or abutment tooth model has a problem that an abutment tooth form originally possessed by the abutment tooth or abutment tooth model is impaired by scanning.

To solve this problem, an object of the present invention is to provide a method of estimating and restoring an abutment tooth form changed by scanning, and a program thereof.

Solution to Problem

A method according to an aspect of the present invention is a method of estimating and restoring a form near a finish line of an abutment tooth or abutment tooth model changed by scanning, the method including:

determining a temporary finish line having multiple points on scan data as an imaginary boundary line between a formed portion and an unformed portion of the abutment tooth or abutment tooth model by creating the scan data including three-dimensional data from raw scan data which is acquired by scanning the abutment tooth or abutment tooth model by a scanner;

deleting the scan data including the temporary finish line in an edge portion of the abutment tooth or abutment tooth model;

extending, in a portion in which the scanned data is deleted, a crown-side temporary finish line and a root-side temporary finish line in directions supplementing the deleted portion of the scan data, respectively; and estimating and restoring the finish line of the edge portion which is formed on the outer side than the edge portion of the deleted scan data based on the extended crown-side temporary finish line and the extended root-side temporary finish line.

Advantageous Effects of Invention

According to the method of estimating and restoring an abutment tooth or an abutment tooth form changed by scanning and the program thereof of the present invention, the abutment tooth or abutment tooth form impaired by scanning can be estimated and restored.

BRIEF DESCRIPTION OF DRAWINGS

FIG. 1 is a flowchart of prosthetic device production using a dental CAD/CAM system;

FIG. 2A is a view of a photograph of an exemplary abutment tooth model;

DESCRIPTION OF EMBODIMENTS

Background of the Present Invention

Figure 2B:
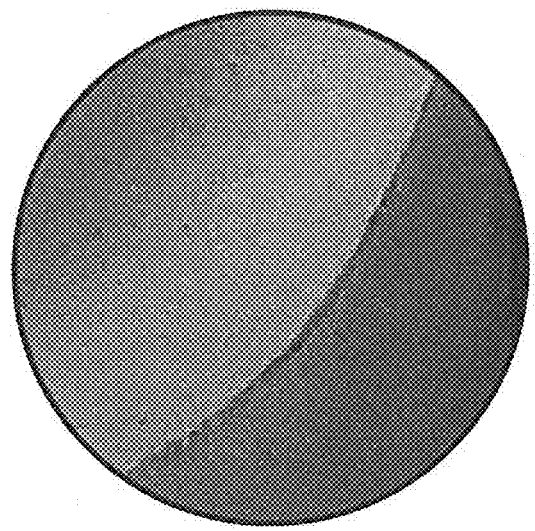
FIG. 2B is an enlarged view of an edge portion of the abutment tooth model of FIG. 2A.

To create prosthetic device design data that is data on a dental CAD used for design of a prosthetic device from raw scan data of an abutment tooth or abutment tooth model in fabrication of a prosthetic device to which a digital dental instrument is applied, steps are roughly classified into two methods.

In one method, after an impression is extracted with an impression material in the patient's oral cavity and plaster is poured therein to fabricate a model, an adjustment etc. are made to a portion requiring fabrication of a prosthetic device without impairing a preparation shape to prepare an abutment tooth model for scanning. This abutment tooth model is scanned by a dental scanning device to acquire point group data, which is read into dental CAD to reproduce an abutment tooth model shape. By using this reproduced abutment tooth model shape as design data of the prosthetic device, a finish line is determined automatically, manually, or both automatically and manually, and is used for designing the prosthetic device together with the design data of the prosthetic device.

In another method, an abutment tooth in the patient's oral cavity is directly scanned by an intraoral scanning device and the acquired data is directly read into the dental CAD before the finish line is determined as in the procedure described above and is used for designing the prosthetic device together with the design data of the prosthetic device.

The data acquired by scanning the abutment tooth model or the abutment tooth in the patient's oral cavity is a group of points, and the dental CAD often retains a scanned shape in a format such as STL data or polygon data based on this data.

Since the points are plotted without considering the presence/absence of an edge at the time of scanning of the abutment tooth model, when the scanned shape is reproduced by the dental CAD, a sharp edge is not directly reproduced and is rounded.

Additionally, when the abutment tooth model is made of plaster and a scanner using laser light is used, a laser beam applied for scanning is considerably transmitted through the plaster, and therefore, especially at a portion with a sharp angle such as an edge, a large proportion of the laser beam is transmitted through the model. This leads to a reduction in amount of light returning to a sensor of the scanning device, so that positional accuracy of a point tends to decrease in a portion such as an edge.

Even in the case of directly scanning the patient's abutment teeth, a problem of rounding of an edge exists as in the case of scanning the abutment tooth model. Additionally, the tooth serving as the abutment tooth is semitransparent, and therefore, even when the scanning light is applied, a portion thereof is transmitted through without being reflected, and scan accuracy further decreases as a light reception amount becomes smaller. Especially at the edge portion, the positional accuracy decreases as in the case of scanning of the abutment tooth model. Furthermore, when the finish line of the abutment is under a gingival margin, projection and reception of the scanning light tend to be difficult, so that the accuracy more significantly decreases. Also when three-dimensional data is acquired from a photograph or a moving image, the shape of the edge portion is rounded in the same way.

Because of these multiple reasons, the shape on the dental CAD which is reproduced from the scan data has a problem that particularly the edge of the finish line is different from the original position and is rounded as compared to the original sharp shape, resulting in a decrease in shape reproduction accuracy in general.

Even if a finish line is determined automatically, manually, or both automatically and manually, from the shape data on the dental CAD configured through such a process, the line is determined on the data having a corner of the edge already rounded and therefore becomes positionally significantly different from the finish line originally possessed by the abutment tooth and the abutment tooth model. In other words, the finish line is determined at a wrong position. It is known that such a decrease in accuracy occurs not only particularly in a sharp edge portion such as a finish line but also in a wide range of angles.

Furthermore, a difference of about 0.03 mm to 0.180 mm is generated between the finish line originally possessed by the abutment tooth or abutment tooth model and the finish line determined by the dental CAD. This is a significant difference equal to or greater than 0.03 mm to 0.04 mm, which is a reference of a visually confirmable gap between the abutment tooth or abutment tooth model and the prosthetic device.

For example, when the angle of the edge of the abutment tooth model is 60 degrees and the shape is reproduced from the point group data acquired by scanning, an error starts from a position at about 0.18 mm shifted from the edge in the inward direction of the abutment tooth model, and the edge is not formed into a sharp shape and is reproduced as a curved surface.

For example, even when the edge angle of the abutment tooth model is 90 degrees, an error starts from a position at about 0.15 mm shifted from the edge in the inward direction of the abutment tooth model, and the edge is reproduced as a curved surface rather than a sharp shape as in the case of the angle of 60 degrees.

Even in the case of the angle of 120 degrees, which is a considerably broad shape for the finish line of the abutment tooth model and generally recognized as an angle hardly causing rounding of the edge, an error starts from a position at about 0.15 mm shifted from the edge in the inward direction of the abutment tooth model as in the case of the angle of 90 degrees, and the edge is reproduced as a curved surface rather than a sharp shape.

As described above, when the edge angle of the finish line of the abutment tooth model is in a rage of the angle of 60 degrees to 120 degrees frequently seen in clinical practice, the generated error is as large as 0.15 mm to 0.18 mm. When the shape is used as a reference shape for designing a shape of a prosthetic device without making any correction to this error, an error easily reaching 0.1 mm or more is included between the finish line original possessed by the abutment tooth model and the finish line of the designed prosthetic device. Additionally, a shape near a margin of the prosthetic device differs from the original shape to be formed. The margin means the periphery of the prosthetic device.

Although it is generally desirable that a space between the abutment teeth and the margin of the prosthetic device is 0.02 mm or more and 0.04 mm or less, the example described above largely deviates therefrom.

In a metal cast crown, a space between the abutment tooth and the margin of the prosthetic device adjusted by a dentist or dental technician and suitably fitting without a problem in practical use is about 0.02 mm to 0.04 mm.

If the space is narrower than 0.02 mm, excess cement cannot overflow at the time of luting of the prosthetic device to the abutment tooth with cement, which may cause an obstacle for fitting. If the space is larger than 0.04 mm, it is extremely difficult to fix the prosthetic device at the correct position, height, and orientation due to the large space when the prosthetic device is mounted on the abutment tooth.

If the design data of the prosthetic device with a rounded edge and the finish line present at a wrong position are directly accepted for designing, processing, and producing the prosthetic device, this may consequently lead to:

poor fitting of the prosthetic device to the abutment tooth or abutment tooth model due to occurrence of a large error;

an influence on a subsequent work, i.e., a cement space of the prosthetic device different from a design value;

an occlusal vertical dimension made higher than a design value; and a portion not formed into the same shape as the designed shape.

They may cause an occurrence of an unintentional thin-wall portion and a risk of fracture during try-in.

Dental technicians generally cautiously adjust margin potions of prosthetic devices with great care so as to prevent occurrence of such problems as much as possible and are compelled to use skills and spend large amounts of time and effort for finishing.

On the other hand, at the time of try-in to a patient of the prosthetic device having a margin peripheral portion made extremely thin as a result of adjustment, the dentist often easily fractures this thin periphery unless carefully performed, so that the device must be remanufactured, and patients, dentists, and dental technicians all must spend extra time and effort in some cases even now.

Therefore, to solve these problems, the present inventors conceive the following invention.

A method according to an aspect of the present invention is a method of estimating and restoring a form near a finish line of an abutment tooth or abutment tooth model changed by scanning, the method including:

determining a temporary finish line having multiple points on scan data as an imaginary boundary line between a formed portion and an unformed portion of the abutment tooth or abutment tooth model by creating the scan data including three-dimensional data from raw scan data which is acquired by scanning the abutment tooth or abutment tooth model by a scanner;

deleting the scan data including the temporary finish line in an edge portion of the abutment tooth or abutment tooth model;

extending, in a portion in which the scanned data is deleted, a crown-side temporary finish line and a root-side temporary finish line in directions supplementing the deleted portion of the scan data, respectively; and estimating and restoring the finish line of the edge portion which is formed on the outer side than the edge portion of the deleted scan data based on the extended crown-side temporary finish line and the extended root-side temporary finish line.

In the method, the determining the temporary finish line may include annularly determining the temporary finish line along the edge portion of the scan data of the abutment tooth or abutment tooth model; and the deleting the scan data may include detecting a crown-side cutting reference point and a root-side cutting reference point based on curvature of the temporary finish line on each of cut sections which is acquired by cutting the scan data of the abutment tooth or abutment tooth model at each of the multiple points of the temporary finish line on the scan data, along a plane including an arbitrary straight line extending from the root side to the crown side in a range surrounded by the temporary finish line, where the crown-side cutting reference point and the root-side cutting reference point serve as reference points for deleting the scan data in the edge portion, creating a crown-direction cutting line by connecting the crown-side cutting reference points of the respective cut sections, creating a root-direction cutting line by connecting the root-side cutting reference points of the respective cut sections, and deleting the scan data in the edge portion between the crown-direction cutting line and the root-direction cutting line;

the extending may include extending, in a portion in which the scanned data is deleted on each of the cut sections, the crown-side temporary finish line from the crown-side cutting reference point in a direction opposite to a crown direction and the root-side temporary finish line from the root-side cutting reference point in a direction opposite to a root direction; and the estimating and restoring the finish line may include calculating an intersection point at which the extended crown-side temporary finish line intersects with the extended root-side temporary finish line in the portion in which the scanned data is deleted on each of the cut sections, and estimating and restoring the finish line in the edge portion of the abutment tooth or abutment tooth model based on an intersection line which is created by connecting the intersection points which are calculated on the respective cut sections, the extended crown-side temporary finish line, and the extended root-side temporary finish line.

In the method, the detecting the crown-side cutting reference point and the root-side cutting reference point may include detecting as the crown-side cutting reference point a first point at which the curvature of the temporary finish line in the crown direction becomes zero or a first point at which a radial direction of the curve thereof is reversed, and detecting as the root-side cutting reference point a first point at which the curvature of the temporary finish line in the root direction becomes zero or a first point at which a radial direction of the curve thereof is reversed, on the cut section.

In the method, the extending may include extending the crown-side temporary finish line while maintaining the curvature, or a change ratio of the curvature, of the temporary finish line near the crown-side cutting reference point, and extending the root-side temporary finish line while maintaining the curvature, or a change ratio of the curvature, of the temporary finish line near the root-side cutting reference point.

In the method, the curvature, or a change ratio of the curvature, of the temporary finish line near the crown-side cutting reference point may include the curvature or a change ratio of the curvature calculated based on the temporary finish line within a range of 0.1 mm from the crown-side cutting reference point in the crown direction; and the curvature or a change ratio of the curvature calculated based on multiple points near the root-side cutting reference point may include the curvature or a change ratio of the curvature calculated based on the temporary finish line within a range of 0.12 mm from the root-side cutting reference point in the root direction.

In the method, the calculating the intersection point may include comparing a first intersection point and a second intersection point, where the first intersection point is calculated by extending the crown-side temporary finish line while maintaining the curvature of the temporary finish line near the crown-side cutting reference point and extending the root-side temporary finish line while maintaining the curvature of the temporary finish line near the root-side cutting reference point, and the second intersection point is calculated by extending the crown-side temporary finish line while maintaining a change ratio of the curvature of the temporary finish line near the crown-side cutting reference point and extending the root-side temporary finish line while maintaining a change ratio of the curvature of the temporary finish line near the root-side cutting reference point, and calculating a point at an outermost position from a tooth crown out of the first intersection point and the second intersection point as the intersection point at which the extended crown-side temporary finish line intersects with the extended root-side temporary finish line.

In the method, a distance between the multiple adjacent points of the temporary finish line which is used for estimating and restoring the finish line may be within a range of 0.002 mm to 1 mm.

The method may include distinguishing in the temporary finish line between a portion in which the finish line is estimated and restored and a portion in which the finish line is not estimated or restored, based on the curvature of an edge of the temporary finish line in each of the cut sections, and determining the temporary finish line as the finish line in the portion in which the finish line is not estimated or restored.

A program according to an aspect of the present invention is executed by a computer, based on the methods.

A non-transitory computer-readable storage medium according to an aspect of the present invention is executed by a computer, based on the methods.

A prosthetic device manufacturing system according to an aspect of the present invention is a manufacturing system of estimating and restoring an abutment tooth form which is changed by scanning to fabricate a prosthetic device fitting to an abutment tooth or an abutment tooth model based on the estimated and restored abutment tooth form, the system including a control device estimating and restoring a finish line based on raw scan data of the abutment tooth or abutment tooth model and creating design data of the prosthetic device from the estimated and restored finish line; and a cutting device fabricating the prosthetic device based on the design data, wherein, the control device has one or more processors, and a memory having stored thereon instructions executable by the one or more processors to cause the processor to perform functions including determining a temporary finish line having multiple points as an imaginary boundary line between a formed portion and an unformed portion of the abutment tooth or abutment tooth model by creating scan data including three-dimensional data from raw scan data which is acquired by scanning the abutment tooth or abutment tooth model by a scanner, deleting the scan data including the temporary finish line in an edge portion of the abutment tooth or abutment tooth model, extending, in a portion in which the scanned data is deleted, a crown-side temporary finish line and a root-side temporary finish line in directions supplementing the deleted portion of the scan data, respectively, and estimating and restoring the finish line of the edge portion which is formed on the outer side than the edge portion of the deleted scan data based on the extended crown-side temporary finish line and the extended root-side temporary finish line.

In the manufacturing system, the determining the temporary finish line may include annularly determining the temporary finish line along the edge portion of the scan data of the abutment tooth or abutment tooth model;

the deleting the scan data may include detecting a crown-side cutting reference point and a root-side cutting reference point based on curvature of the temporary finish line on each of cut sections which is acquired by cutting the scan data of the abutment tooth or abutment tooth model at each of the multiple points of the temporary finish line on the scan data, along a plane including an arbitrary straight line extending from the root side to the crown side in a range surrounded by the temporary finish line, where the crown-side cutting reference point and the root-side cutting reference point serve as reference points for deleting the scan data in the edge portion creating a crown-direction cutting line by connecting the crown-side cutting reference points of the respective cut sections, creating a root-direction cutting line by connecting the root-side cutting reference points of the respective cut sections, and deleting the scan data in the edge portion between the crown-direction cutting line and the root-direction cutting line;

the extending may include extending, in a portion in which the scanned data is deleted on each of the cut sections, the crown-side temporary finish line from the crown-side cutting reference point in a direction opposite to a crown direction and the root-side temporary finish line from the root-side cutting reference point in a direction opposite to a root direction; and the estimating and restoring the finish line may include calculating an intersection point at which the extended crown-side temporary finish line intersects with the extended root-side temporary finish line in the portion in which the scanned data is deleted on each of the cut sections, and estimating and restoring the finish line in the edge portion of the abutment tooth or abutment tooth model based on an intersection line which is created by connecting the intersection points which are calculated on the respective cut sections, the extended crown-side temporary finish line, and the extended root-side temporary finish line.

In the manufacturing system, the detecting the crown-side cutting reference point and the root-side cutting reference point may include detecting as the crown-side cutting reference point a first point at which the curvature of the temporary finish line in the crown direction becomes zero or a first point at which a radial direction of a curve is reversed, and detecting as the root-side cutting reference point a first point at which the curvature of the temporary finish line in the root direction becomes zero or a first point at which a radial direction of a curve is reversed, on the cut section.

In the manufacturing system, the extending may include
extending the crown-side temporary finish line while maintaining the curvature, or a change ratio of the curvature, of the temporary finish line near the crown-side cutting reference point, and extending the root-side temporary finish line while maintaining the curvature, or a change ratio of the curvature, of the temporary finish line near the root-side cutting reference point.

In the manufacturing system,
the curvature, or a change ratio of the curvature, of the temporary finish line near the crown-side cutting reference point may include the curvature or a change ratio of the curvature which is calculated based on the temporary finish line within a range of 0.1 mm from the crown-side cutting reference point in the crown direction; and the curvature or a change ratio of the curvature which is calculated based on multiple points near the root-side cutting reference point may include the curvature or a change ratio of the curvature which is calculated based on the temporary finish line within a range of 0.12 mm from the root-side cutting reference point in the root direction.

In the manufacturing system, the calculating the intersection point may include comparing a first intersection point and a second intersection point, where the first intersection point is calculated by extending the crown-side temporary finish line while maintaining the curvature of the temporary finish line near the crown-side cutting reference point and extending the root-side temporary finish line while maintaining the curvature of the temporary finish line near the root-side cutting reference point, and the second intersection point is calculated by extending the crown-side temporary finish line while maintaining a change ratio of the curvature of the temporary finish line near the crown-side cutting reference point and extending the root-side temporary finish line while maintaining a change ratio of the curvature of the temporary finish line near the root-side cutting reference point, and calculating a point at an outermost position from a tooth crown out of the first intersection point and the second intersection point as the intersection point at which the extended crown-side temporary finish line intersects with the extended root-side temporary finish line.

In the manufacturing system, a distance between the multiple adjacent points of the temporary finish line which is used for estimating and restoring the finish line may be within a range of 0.002 mm to 1 mm.

In the manufacturing system,
the instruction may include distinguishing in the temporary finish line between a portion in which the finish line is estimated and restored and a portion in which the finish line is not estimated or restored, based on the curvature of an edge of the temporary finish line in each of the cut sections, and determining the temporary finish line as the finish line in the portion in which the finish line is not estimated or restored.

A prosthetic device manufacturing method according to an aspect of the present invention is a manufacturing method of estimating and restoring an abutment tooth form which is changed by scanning to fabricate a prosthetic device fitting to an abutment tooth or an abutment tooth model based on the estimated and restored abutment tooth form, the method including acquiring raw scan data of the abutment tooth or abutment tooth model;

determining a temporary finish line having multiple points as an imaginary boundary line between a formed portion and an unformed portion of the abutment tooth or abutment tooth model by creating scan data including three-dimensional data from the raw scan data;

deleting the scan data including the temporary finish line in an edge portion of the abutment tooth or abutment tooth model;

extending, in the portion in which the scanned data is deleted, a crown-side temporary finish line and a root-side temporary finish line in directions supplementing the deleted portion of the scan data, respectively;

estimating and restoring the finish line of the edge portion which is formed on the outer side than the edge portion of the deleted scan data based on the extended crown-side temporary finish line and the extended root-side temporary finish line; and fabricating the prosthetic device from design data created based on the finish line.

The present invention will now be described with reference to the drawings. In all of the following figures, the same or corresponding portions are denoted by the same reference numerals, and will not redundantly be described.

First Embodiment

[Flow of Prosthetic Device Production]

FIG. 1 is an exemplary flowchart of prosthetic device production using a dental CAD/CAM system. As shown in FIG. 1, the prosthetic device production using a dental CAD/CAM system includes an abutment tooth forming step ST1, a scanning step ST2, a design data creating step ST3, and a prosthetic device fabricating step ST4.

At the abutment tooth forming step ST1, an abutment tooth is formed. In this description, an abutment tooth is a tooth which is formed by a dentist so that a prosthetic device is stably mounted thereon. In the case of dental caries and/or abnormal contact, etc., the affected part is remove/filled before forming the abutment tooth. For example, the abutment tooth is formed by grinding down a natural tooth with a cutting device. Alternatively, the abutment tooth is formed by inserting a metal bar or a bar of glass fiber into a tooth, constructing an object by using a paste such as a resin material, and grinding down the object with a cutting device.

The prosthetic device which is covered by the present invention is a dental prosthetic device such as inlays, onlays, crowns, bridges, dentures, implant superstructures, etc. mounted for restoring a shape and a function by an artifact onto a tooth having an affected part lost or partly lost due to fracture or tooth extraction because of a tooth disease such as dental caries and periodontal diseases, an accident, injury, etc., mainly in a dental field.

At the scanning step ST2, the shape of the abutment tooth which is formed at the abutment tooth forming step ST1 is scanned by a scanning device etc. For example, the scanning of the abutment tooth may be performed by fabricating an abutment tooth model and scanning the abutment tooth model, or by directly scanning the abutment tooth in the oral cavity. The abutment tooth model is a model acquired by imprinting a formed abutment tooth with an impression material to fabricate a female mold of a patient's abutment tooth and surrounding gingiva, pouring plaster etc. into the female mold, taking out the cured plaster to duplicate a site requiring treatment by the prosthetic device in the patient's oral cavity. In the first embodiment, an abutment tooth model is fabricated and the abutment tooth model is scanned.

Figure 3A:
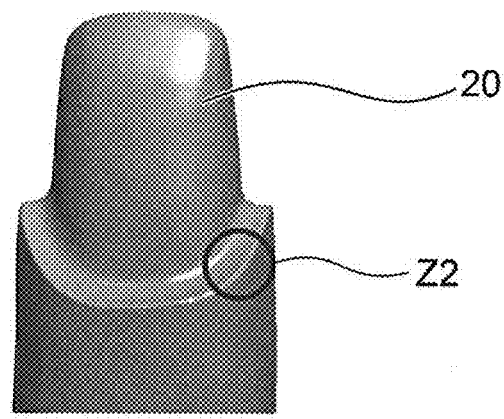
FIG. 3A is a view of an exemplary scan data that is acquired by scanning the abutment tooth model of FIG. 2A and that has an originally-possessed abutment tooth form impaired.
Figure 3B:
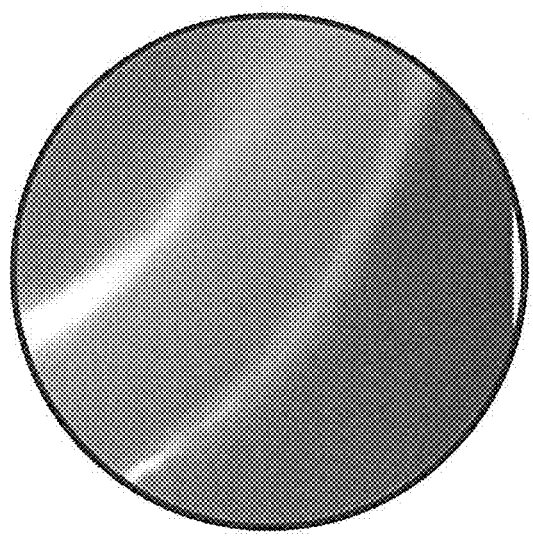
FIG. 3B is an enlarged view of an edge portion of the abutment tooth model of FIG. 3A.

FIG. 2A shows a photograph of an exemplary abutment tooth model 10. FIG. 2B shows an enlarged view of an edge portion Z1 of the abutment tooth model 10 of FIG. 2A. FIG. 3A shows exemplary scan data 20 which is acquired by scanning the abutment tooth model 10 of FIG. 2A. FIG. 3B shows an enlarged view of an edge portion Z2 of the scan data 20 of FIG. 3A. As shown in FIGS. 2A and 3A, at the scanning step ST2, the abutment tooth model 10 shown in FIG. 2A is scanned by a scanning device to acquire the scanning data 20 as STL data shown in FIG. 3A. The edge portion Z1 of the abutment tooth model 10 shown in FIG. 2A is compared with the edge portion Z1 of the scan data 20 shown in FIG. 3A. As shown in FIGS. 2B and 3B, a form originally possessed by a finish line portion of the abutment tooth model 10 shown in FIG. 2B is obviously impaired in a finish line portion of the scan data 20 shown in FIG. 3B.

In the design data creating step ST3, design data of the prosthetic device is created based on the scan data 20 of the abutment tooth which is acquired at the scanning step ST2. Specifically, the scan data 20 of the abutment tooth is read into the dental CAD, and the shape of the abutment tooth is reproduced. Based on this reproduced shape of the abutment tooth, the design data of the prosthetic device is created.

At the design data creating step ST3, a method of estimating and restoring an abutment tooth form near a finish line which is changed by scanning according to the present invention is implemented. In this description, the finish line means a boundary line between a formed portion and an unformed portion of the abutment tooth or abutment tooth model. The formed portion means a portion having a shape intentionally adjusted at the tooth crown part by a dentist or a dental technician for mounting the dental prosthesis. The unformed portion means a portion where the shape of the abutment tooth or abutment tooth model 10 is left as it is without change on the tooth root portion side. In other words, the finish line corresponds to a portion in contact with an edge of the prosthetic device (coping) on the peripheral shape of the abutment tooth or abutment tooth model and is a line serving as an end portion of the prosthetic device when the device is disposed.

At the prosthetic device fabricating step ST4, the prosthetic device is fabricated based on the design data created at the design data creating step ST3. Specifically, based on the design data, the inner side of the prosthetic device is ground down by a cutting device so as to fit to the shape of the abutment tooth model 10.

Figure 4:
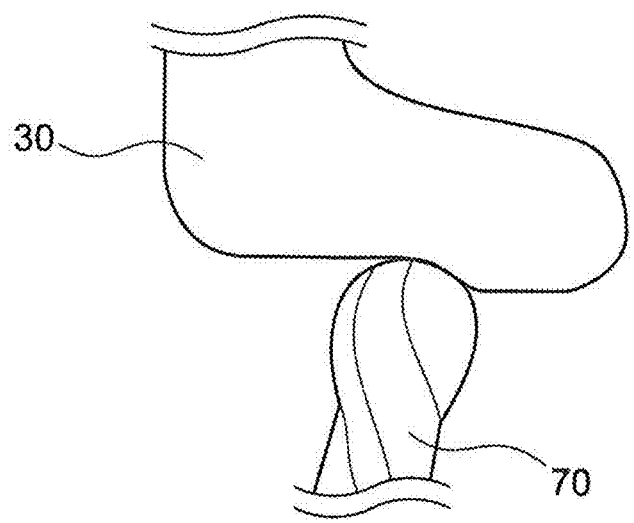
FIG. 4 is a diagram of an exemplary production step of a prosthetic device.

FIG. 4 shows a fabricating step of an exemplary prosthetic device 30. As shown in FIG. 4, the inner side of the prosthetic device 30 is cut by a cutting device 70. As a result, the inner side of the prosthetic device 30 can be formed into a shape fitting to the shape of the abutment tooth model 10.

Figure 5:
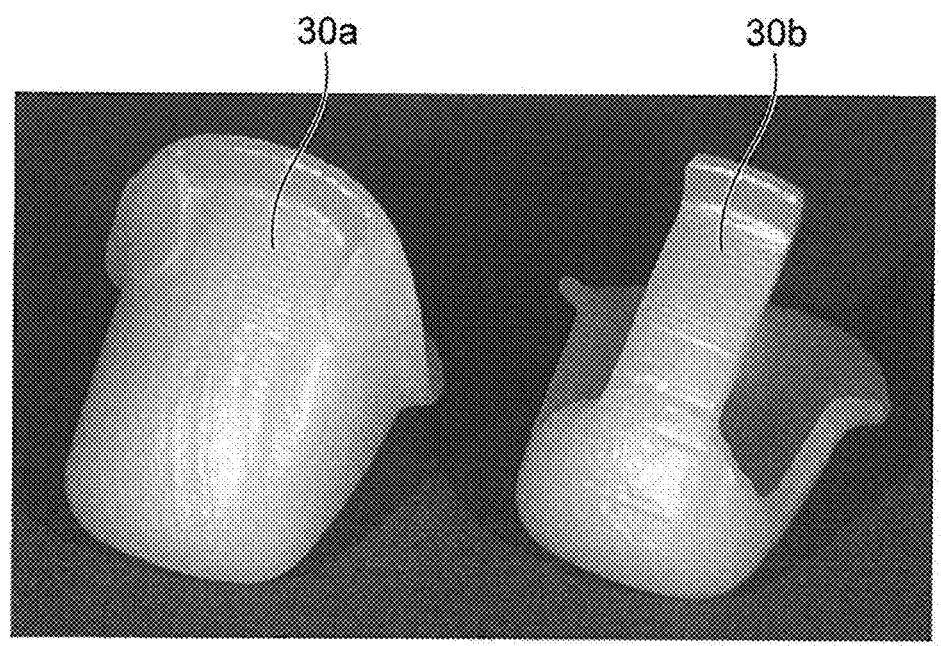
FIG. 5 is a view of a photograph of an exemplary prosthetic device.

FIG. 5 shows photographs of exemplary prosthetic devices 30a and 30b. In FIG. 5, the two fabricated prosthetic devices (copings) 30a and 30b are shown. The prosthetic device 30b has a portion of a side wall cut so that a fitting state of the inner shape to the abutment tooth model is easily seen.

Figure 6:
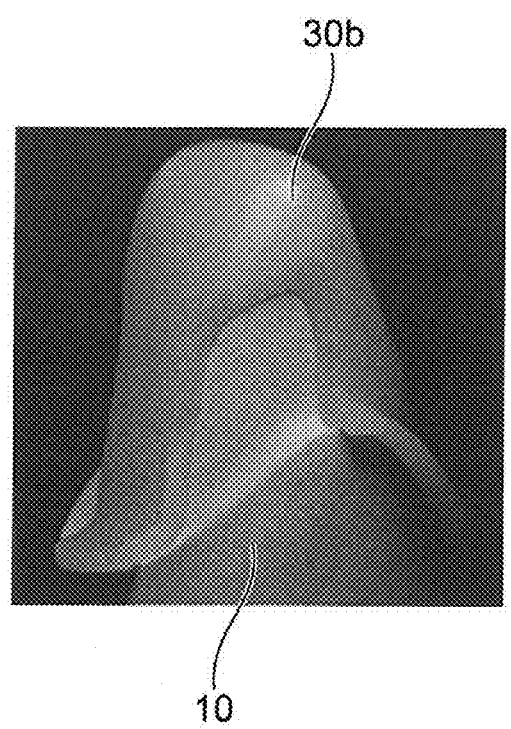
FIG. 6 is a view of a photograph of a state in which a prosthetic device is attached to an abutment tooth model.

FIG. 6 shows a photograph of a state in which the prosthetic device 30b is attached to the abutment tooth model 10. In FIG. 6, the prosthetic device 30b with the partially cut side wall is attached to the abutment tooth model 10.

In this way, in the production of the prosthetic device using the dental CAD/CAM system, the abutment tooth forming step ST1, the scanning step ST2, the design data creating step ST3, and the prosthetic device fabricating step ST4 are executed to fabricate the prosthetic device 30. The flowchart of the prosthetic device production shown in FIG. 1 is an example, and the present invention is not limited to these steps.

[Method of Estimating and Restoring Abutment Tooth Form]

A method of estimating and restoring an abutment tooth form which is changed by scanning according to the present invention will be described. Specifically, description will be made of a method of estimating and restoring as the abutment tooth form a shape near the finish line of the abutment tooth or abutment tooth model and the finish line.

Figure 7:
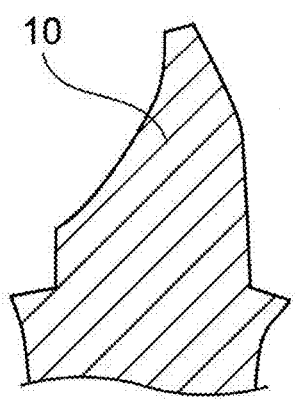
FIG. 7 is a cross-sectional view of an abutment tooth model.
Figure 8:
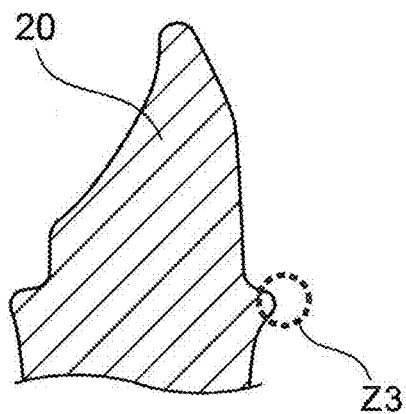
FIG. 8 is a view of scan data of the cross-sectional shape of the abutment tooth model of FIG. 7.

FIG. 7 shows a cross-sectional view of the exemplary abutment tooth model 10. FIG. 8 shows the scan data 20 of the cross-sectional shape of the abutment tooth model 10 of FIG. 7. Comparing FIGS. 7 and 8, the sharp edge shape originally possessed by the abutment tooth model 10 shown in FIG. 7 is impaired in the edge portion of the scan data 20 shown in FIG. 8, and the edge portion is roundly formed.

Figure 9:
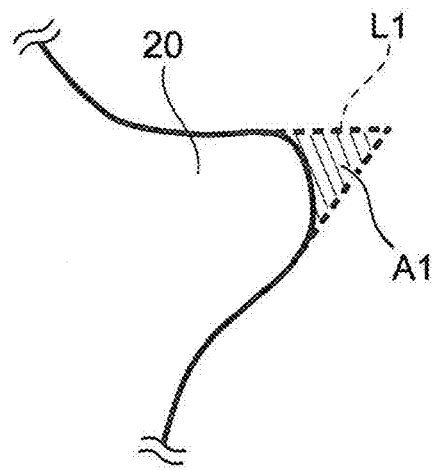
FIG. 9 is a schematic enlarged view of an edge portion of the scan data of FIG. 8.

FIG. 9 shows a schematic enlarged view of an edge portion Z3 of the scan data 20 of FIG. 8. A line L1 shown in FIG. 9 shows a contour of an edge of the actual abutment tooth model 10. As shown in FIG. 9, the shape of the abutment tooth model 10 which is reproduced by the scan data 20 is formed such that the shape has disappeared in a region A1 where the edge is originally formed. Therefore, the shape of the abutment tooth model 10 reproduced by the scan data 20 is roundly formed in the edge portion as compared to the shape of the actual abutment tooth model 10.

Figure 10:
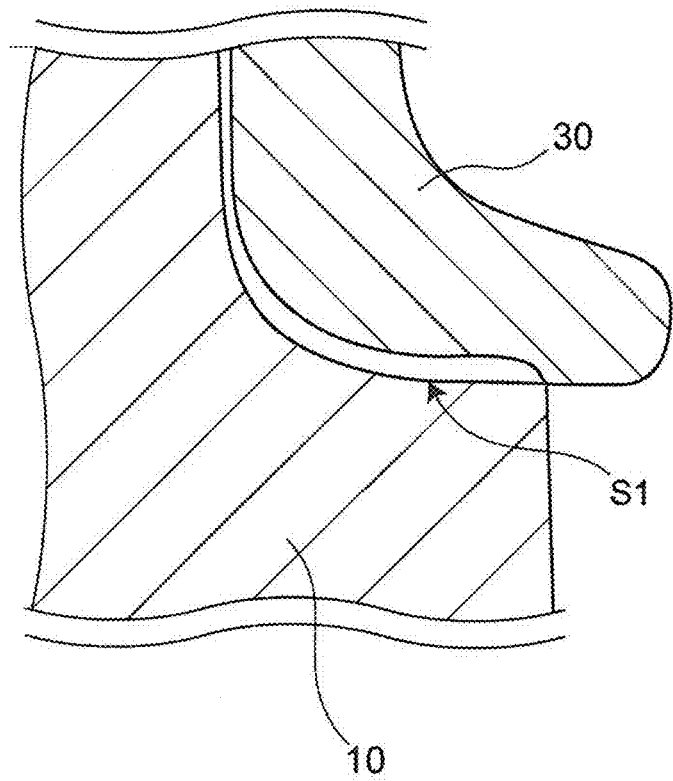
FIG. 10 is an enlarged schematic partial cross-sectional view of an edge portion when a prosthetic device fabricated based on the scan data of FIG. 8 is attached to the abutment tooth model.

FIG. 10 shows as a reference example a schematic enlarged view of the edge portion when the prosthetic device 30 fabricated based on the scan data 20 of FIG. 8 is attached to the abutment tooth model 10. As shown in FIG. 10, when the prosthetic device 30 which is fabricated by using the scan data 20 with the edge portion having disappeared is attached to the abutment tooth model 10, the edge portion of the abutment tooth model 10 interferes with an inner portion of the prosthetic device 30. Specifically, the prosthetic device 30 abuts on the edge portion of the abutment tooth model 10 and floats up. In this way, if the prosthetic device 30 is fabricated based on the scan data 20 with the edge portion having disappeared, the prosthetic device 30 does not come into close contact with the abutment tooth model 10 and a gap S1 is formed.

Figure 11:
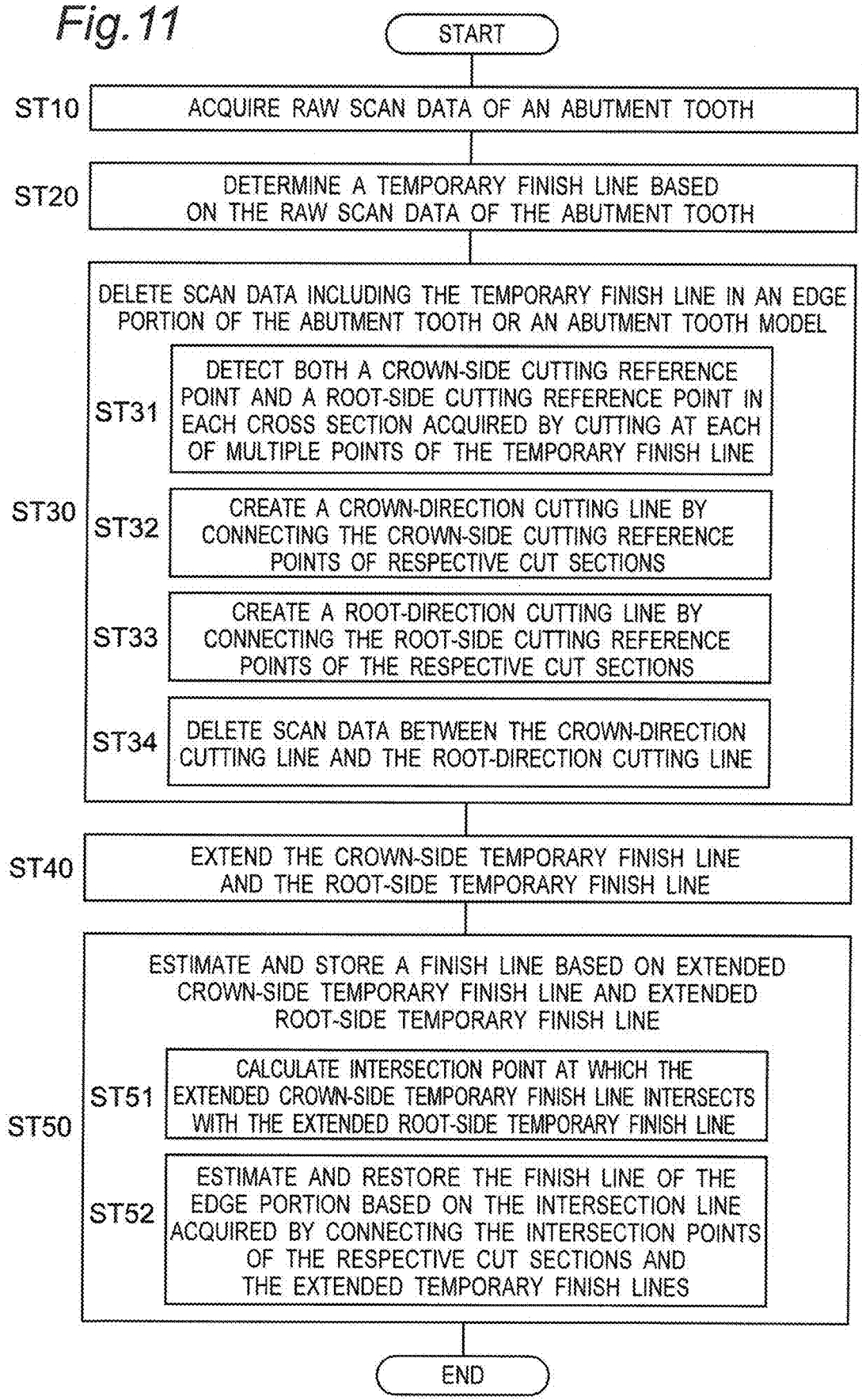
FIG. 11 is a flowchart of a method of estimating and restoring an abutment form changed by scanning according to the present invention.

FIG. 11 shows a flowchart of a method of estimating and restoring an abutment tooth form which is changed by scanning according to the present invention.

As shown in FIG. 11, at step ST10, scan data of an abutment tooth is acquired. For example, raw scan data of the abutment tooth is acquired by an intraoral scanner capable of directly scanning portions in the patient's oral cavity. In the case of the abutment tooth model, raw scan data is acquired by scanning the abutment tooth model which is placed on a stage of a desktop scanner. Alternatively, the abutment tooth model may be scanned by the intraoral scanner even outside the oral cavity to acquire raw scan data. The raw scan data which is acquired in this way is an aggregate of points and is positional information of the points.

The scanning device often provides output in a format of point group data, or STL data which is acquired by adding front and back of a surface and normal vector information of the surface when a triangle constituted by three adjacent points is the surface, or wire frame data composed of triangles which are acquired by connecting adjacent points, or polygon data which is acquired by rendering a surface to each triangle of a wire frame. The STL data is most commonly used in dentistry and is spreading among different manufacturers as highly compatible common format data.

At step ST20, a temporary finish line is determined based on the raw scan data of the abutment tooth or abutment tooth model 10. In this description, the temporary finish line means an imaginary boundary line between the formed portion and the unformed portion of the abutment tooth or abutment tooth model. In other words, the temporary finish line means an imaginary line of the edge portion on the scan data of the abutment tooth or abutment tooth model.

Specifically, at step ST20, the raw scan data is read into a dental CAD used for the purpose of designing a dental prosthetic device to create scan data including three-dimensional data so as to reproduce the abutment tooth, or the shape of the abutment tooth model on the dental CAD.

The scan data including three-dimensional data is data representative of a three-dimensional shape made up of, for example, a parametric curve, a set of point data, a higher-order function, or a combination thereof.

In the first embodiment, the temporary finish line having multiple points is determined based on scan data composed of a parametric curve. Specifically, the dental CAD automatically extracts the temporary finish line according to preset part information or various parameters for extracting the temporary finish line. In the method, points constituting the temporary finish line are obtained according to an arithmetic pitch determined by the user in advance or during operation and, for example, these points are sequentially connected to determine one temporary finish line going around an object part (e.g., edge line).

Figure 12A:
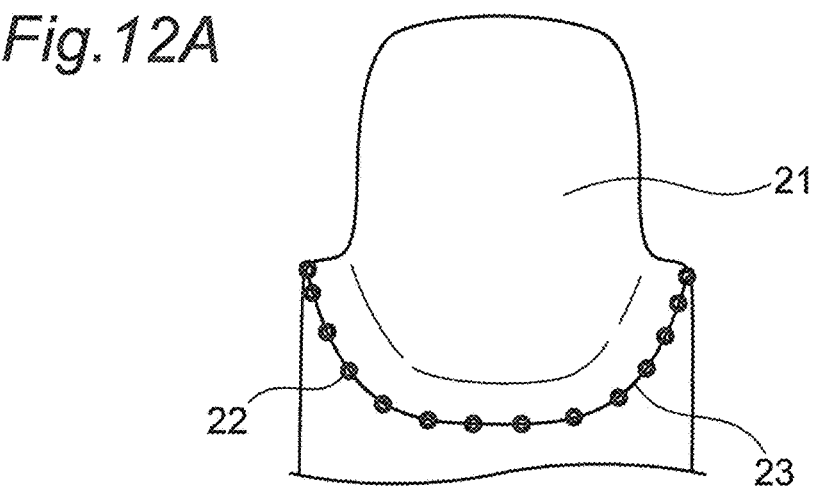
FIG. 12A is a schematic of a step of determining a temporary finish line.

FIG. 12A is a schematic of the step of determining a temporary finish line 23. FIG. 12A shows scan data 21 composed of a parametric curve from the raw scan data. In FIG. 12A, to facilitate understanding of the temporary finish line 23 of the edge line, only multiple points 22 of the edge line in the scan data 21 are shown.

As shown in FIG. 12A, the temporary finish line 23 having the multiple points 22 is determined by creating the scan data 21 composed of a parametric curve from raw scan data. In the first embodiment, the temporary finish line 23 is annularly determined along the edge portion of the scan data 21 of the abutment tooth or abutment tooth model 10. Therefore, in the first embodiment, the temporary finish line 23 is determined as a virtual edge line of the scan data 21.

Returning to FIG. 11, at step ST30, the scan data 21 including the temporary finish line 23 is deleted in the edge portion of the abutment tooth or abutment tooth model 10. Specifically, at step ST30, steps ST31 to ST34 are executed to delete the scan data 21 of the edge portion of the abutment tooth or abutment tooth model 10.

At step ST31, a crown-side cutting reference point and a root-side cutting reference point are detected in each cross section acquired by cutting the scan data 21 at the multiple points 22 of the temporary finish line 23. Specifically, the crown-side cutting reference point and the root-side cutting reference point are detected based on the curvature of the temporary finish line 23 on each of cut sections which is acquired by cutting the scan data 21 at each of the multiple points 22 of the temporary finish line 23 on the scan data 21 of the abutment tooth or abutment tooth model 10, along a plane including an arbitrary straight line extending from the root side to the crown side included in the range surrounded by the temporary finish line 23. The crown side cutting reference point and the root-side cutting reference point are reference points for deleting the scan data 21 in the edge portion and are reference points selected from the multiple points 22 of the temporary finish line 23 on the cut section.

In the first embodiment, the cut section which is cut along a plane including an arbitrary straight line extending from the root side to the crown side in the range surrounded by the temporary finish line 23 is desirably a normal-direction cross section of the temporary finish line 23.

The cut section which is cut along a plane including an arbitrary straight line extending from the root side to the crown side in the range surrounded by the temporary finish line 23 is not limited to the normal-direction cross section of the temporary finish line 23. The cut section cut along a plane including an arbitrary straight line extending from the root side to the crown side included in the range which is surrounded by the temporary finish line 23 may be any cut section cut along a plane extending from the root side toward the crown side and may be, for example, a cut section which is cut along a plane including a tooth axis.

Figure 12B:
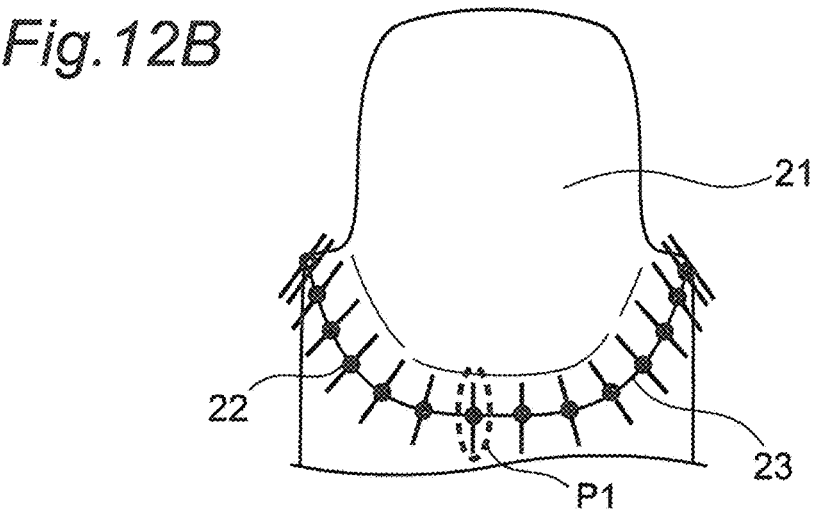
FIG. 12B is a schematic of a cutting position of cutting scan data based on multiple points of the temporary finish line.

FIG. 12B is a schematic of a position at which the scan data 21 is cut based on the multiple points 22 of the temporary finish line 23. As shown in FIG. 12B, at step ST31, the scan data at the multiple points 22 constituting the temporary finish line 23 on the scan data 21 of the abutment tooth or abutment tooth model 10 is cut along a plane including an arbitrary straight line extending from the root side to the crown side in the range surrounded by the temporary finish line 23. For example, at the multiple points 22 constituting the temporary finish line 23, the scan data 21 is cut in a tooth axis direction, the coming-out direction of the tooth crown (crown), or the direction without undercut. In the first embodiment, the temporary finish line 23 is determined over the entire circumference of the edge of the scan data 21. Therefore, the scan data 21 is sequentially cut until a full circle is completed around the edge line from an arbitrary point defined as a starting point out of the multiple points 22 constituting the temporary finish line 23 forming the edge line.

Figure 12C:
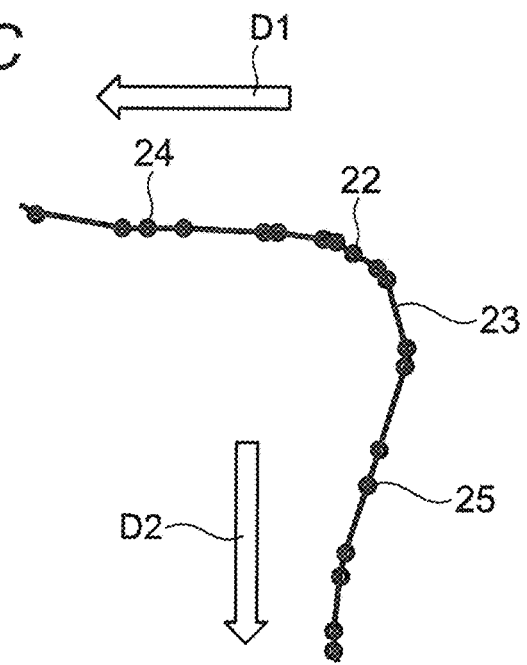
FIG. 12C is a schematic of a step of detecting a crown-side cutting reference point and a root-side cutting reference point on a cut section at a cutting position P1 of FIG. 12B.

FIG. 12C is a schematic view of a step of detecting the crown-side cutting reference point 24 and the root-side cutting reference point 25 on a cut section at a cutting position P1 of FIG. 12B. As shown in FIG. 12C, at step ST31, the crown-side cutting reference point 24 and the root-side cutting reference point 25 are detected on each of the cut sections based on the curvature of the temporary finish line 23 of the cut section. Specifically, on each of the cut sections of the edge portion, the crown-side cutting reference point 24 is acquired by detecting a first point at which the curvature of the temporary finish line 23 in a crown direction D1 becomes zero or a first point at which a radial direction of the curve thereof is reversed, out of the multiple points 22 of the temporary finish line 23 of the cut section. At step ST31, the root-side cutting reference point 25 is acquired by detecting a first point at which the curvature of the temporary finish line 23 in a root direction D2 becomes zero or a first point at which a radial direction of the curve thereof is reversed, out of the multiple points 22 of the temporary finish line 23 on the cut section.

Returning to FIG. 11, at step ST32, the crown-side cutting reference points 24 of the respective cut sections are connected to create a crown-direction cutting line. Specifically, the crown-direction cutting line is created by connecting the crown-side cutting reference points 24 of the respective cut sections to create a parametric curve.

At step ST33, the root-side cutting reference points 25 of the respective cut sections are connected to create a root-direction cutting line. Specifically, the root-direction cutting line is created by connecting the root-side cutting reference points 25 of the respective cut sections to create a parametric curve.

Figure 12D:
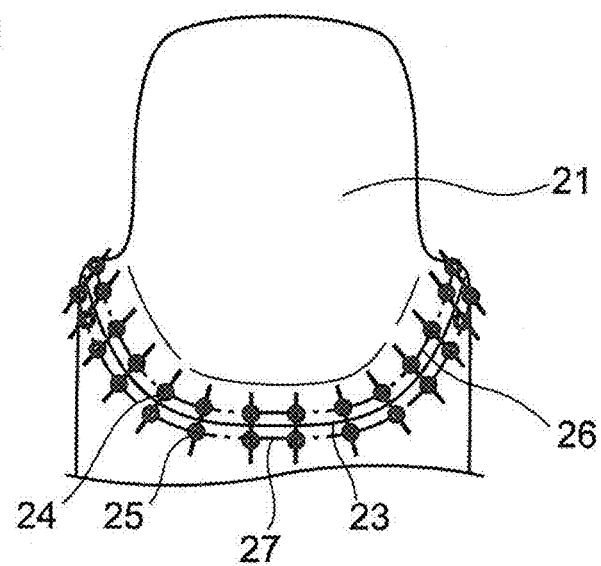
FIG. 12D is a schematic of a step of creating a crown-direction cutting line and a root-direction cutting line.

FIG. 12D is a schematic of a step of creating a crown-direction cutting line 26 and a root-direction cutting line 27. As shown in FIG. 12D, by connecting the crown-side cutting reference points 24 of the respective cut sections to create a parametric curve, the crown-direction cutting line 26 is created on the crown side relative to the temporary finish line 23. By connecting the root-side cutting reference points 25 of the respective cut sections to create a parametric curve, the root-direction cutting line 27 is created on the root side relative to the temporary finish line 23. The crown-directional cutting line 26 and the root-direction cutting line 27 are each created as one curve going around the edge portion.

In the first embodiment, an example of the crown-direction cutting line 26 and the root-direction cutting line 27 which are created by using a parametric curve has been described; however, the present invention is not limited thereto. In addition to a parametric curve, the crown-direction cutting line 26 and the root-direction cutting line 27 may be created with, for example, a set of point data, a higher-order function, or a combination thereof.

Returning to FIG. 11, at step ST34, the scan data 21 of the edge portion is deleted between the crown-direction cutting line 26 and the root-direction cutting line 27. Specifically, the scan data 21 of the edge portion including the temporary finish line 23 is deleted.

Figure 12E:
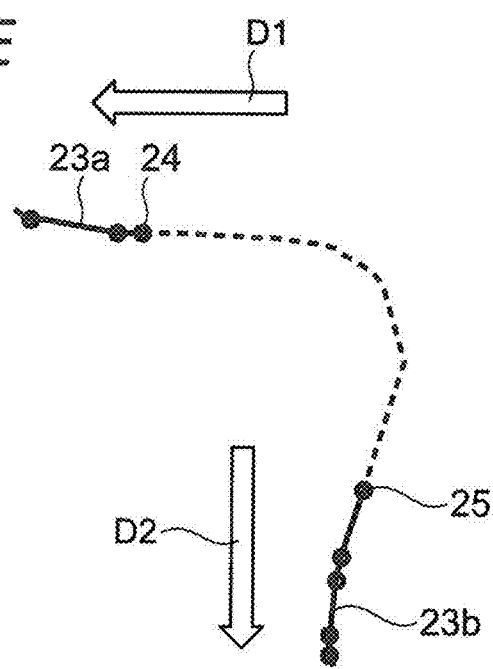
FIG. 12E is a schematic of a step of deleting the edge portion of the scan data.

FIG. 12E is a schematic of a step of deleting the edge portion of the scan data 21 on the cut section. A dotted line shown in FIG. 12E indicates the deleted temporary finish line. As shown in FIG. 12E, the scan data 21 of the edge portion, i.e., the temporary finish line 23 between the crown-side cutting reference point 24 and the root-side cutting reference point 25, is deleted on the cut section. As a result, the line is divided into a crown-side temporary finish line 23a and a root-side temporary finish line 23b.

Returning to FIG. 11, at step ST40, in the deleted portion of the scan data 21 on each of the cut sections, the crown-side temporary finish line 23a is extended in a direction supplementing the deleted portion of the scan data 21, and the root-side temporary finish line 23b is extended in a direction supplementing the deleted scan data. Specifically, at step ST40, in the deleted portion of the scan data 21 on each of the cut sections, the crown-side temporary finish line 23a is extended from the crown-side cutting reference point 24 in the direction opposite to the crown direction D1. In the deleted portion of the scan data 21 on each of the cut sections, the root-side temporary finish line 23b is extended from the root-side cutting reference point 25 in the direction opposite to the root direction D2.

Figure 12F:
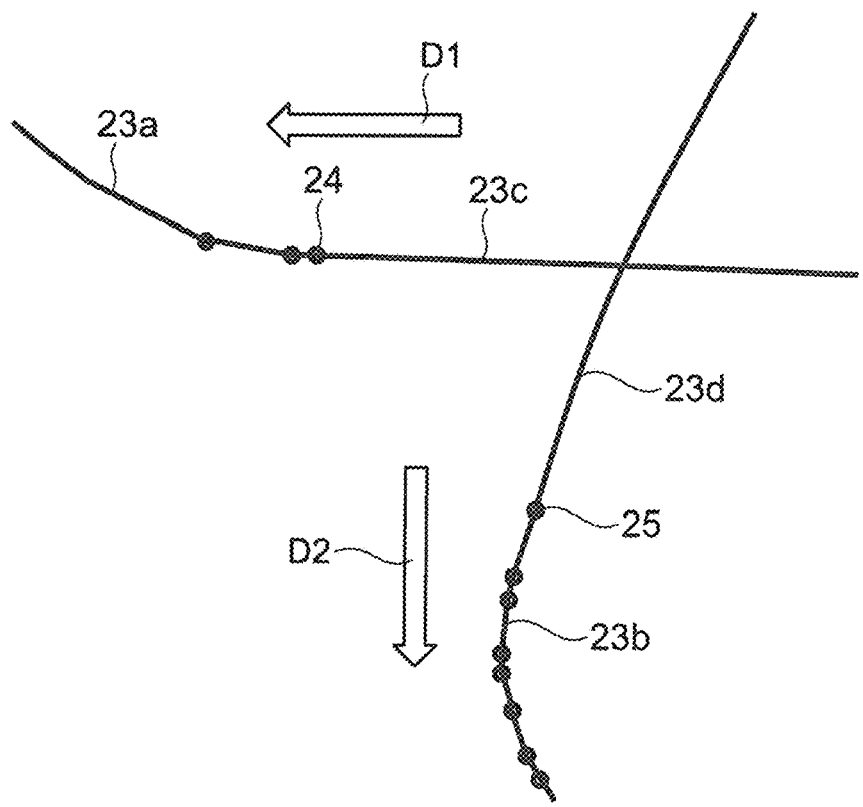
FIG. 12F is a schematic of a step of extending temporary finish lines.

FIG. 12F is a schematic of a step of extending the temporary finish lines 23a, 23b. As shown in FIG. 12F, at step ST40, the crown-side temporary finish line 23a is extended from the crown-side cutting reference point 24 in the direction opposite to the crown direction D1 while maintaining the curvature, or a change ratio of the curvature, of the temporary finish line 23a near the crown-side cutting reference point 24. At step ST40, the root-side temporary finish line 23b is extended from the root-side cutting reference point 25 in the direction opposite to the direction D2 while maintaining the curvature, or a change ratio of the curvature, of the temporary finish line 23b near the root-side cutting reference point 25. As a result, a crown-side temporary finish line 23c extending in the direction supplementing the deleted portion of the scan data 21 from the crown-side is formed along with a root-side temporary finish line 23d extending in the direction supplementing the deleted portion of the scan data 21 from the root-side.

The curvature, or a change ratio of the curvature, of the temporary finish line 23a near the crown-side cutting reference point 24 is preferably the curvature or a change ratio of the curvature calculated based on the temporary finish line 23a within a range of 0.1 mm from the crown-side cutting reference point 24 in the crown direction D1.

Referring to the range of 0.1 mm or more from the crown-side cutting reference point 24 in the crown direction D1 for calculation of the curvature, if the abutment tooth or abutment tooth model 10 has a discontinuous inclination with respect to the finish line, the discontinuous inclination may be included in the reference range. This may impede estimating and restoring the finish line with practically sufficient accuracy.

The curvature, or a change ratio of the curvature, of the temporary finish line 23b near the root-side cutting reference point 25 is preferably the curvature or a change ratio of the curvature calculated based on the temporary finish line 23b within a range of 0.12 mm from the root-side cutting reference point 25 in the root direction D2.

Referring to the range of 0.12 mm or more from the root-side cutting reference point 25 in the root direction D2 for calculation of the curvature, if a portion which is formed by trimming or a portion with a changed inclination angle exists, the portion may also be included in the reference range. This may impede estimating and restoring the finish line with practically sufficient accuracy.

Returning to FIG. 11, at step ST50, the finish line is estimated and restored based on the extended crown-side temporary finish line 23c and the extended root-side temporary finish line 23d. Specifically, at step ST50, the finish line is estimated and restored by executing steps ST51 and ST52.

At step ST51, an intersection point is calculated at which the extended crown-side temporary finish line 23c intersects with the extended root-side temporary finish line 23d.

Figure 12G:
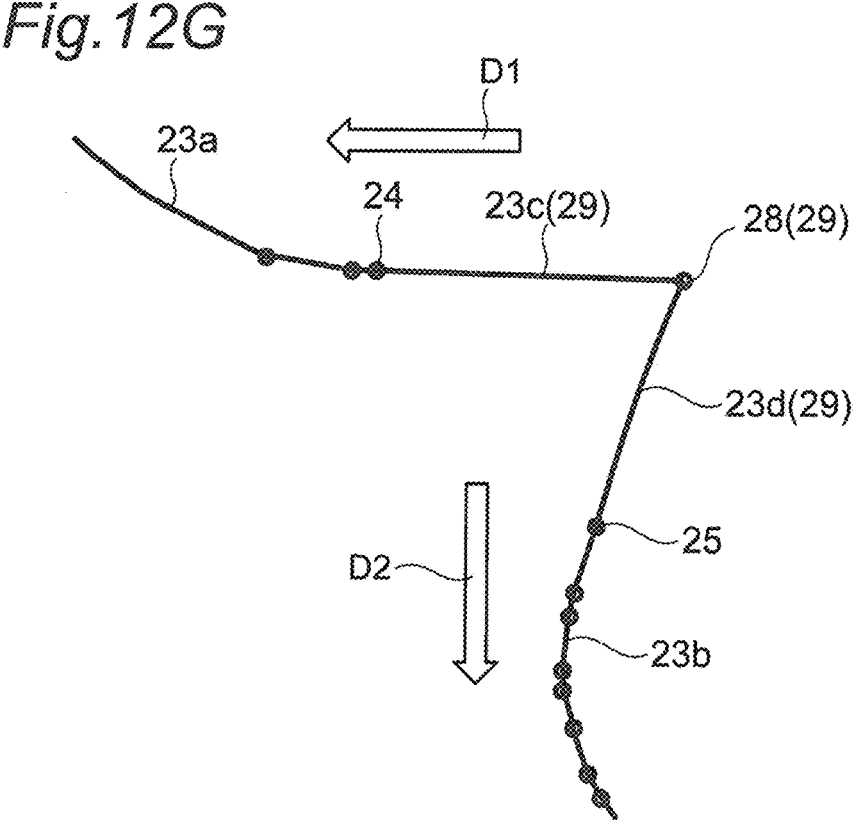
FIG. 12G is a schematic of a step of calculating an intersection point of the extended temporary finish lines.

FIG. 12G is a schematic of a step of calculating an intersection point 28 of the extended temporary finish lines 23c and 23d. As shown in FIG. 12G, at step ST51, the intersection point 28 is calculated at which the extended crown-side temporary finish line 23c intersects with the extended root-side temporary finish line 23d, and surplus lines projecting outward beyond the intersection point 28 are trimmed off.

Returning to FIG. 11, at step ST52, a finish line 29 in the edge portion is estimated and restored based on an intersection line which is acquired by connecting the intersection points 28 of the respective cut sections and the extended temporary finish lines 23c and 23d. Specifically, the intersection line is acquired by connecting the intersection points 28 of the respective cut sections. The intersection line corresponds to the actual edge of the abutment tooth or abutment tooth model and is created as one curve. At step ST52, this intersection line is estimated and restored as the finish line forming the edge of the abutment tooth or abutment tooth model. At step ST52, the extended crown-side temporary finish line 23c and the extended root-side temporary finish line 23d which are connected to the intersecting line on each of the cut sections are also estimated and restored as the finish line forming the edge portion of the abutment tooth or abutment tooth model.

In the first embodiment, the intersection line is created with, for example, a parametric curve, a set of point data, a higher-order function, or a combination thereof.

A distance between the multiple adjacent points 22 of the temporary finish line 23 which is used for estimating and restoring the finish line 29 is within a range of 0.002 mm to 1 mm, preferably within a range of 0.002 mm to 0.250 mm.

When the distance between two adjacent points of the multiple points 22 is smaller than 0.002 mm, the distance between the two adjacent points becomes smaller than the scan pitch and the number of processing points increases, while no improvement is expected in accuracy of the finish line estimated and restored in the present invention. Even when finely scanned, a distance between the points of the scan data 21 is about 0.005 mm, and an error is inevitably included because of complement with lines and curves. This error is at least about 0.002 mm.

Furthermore, the surface of the abutment tooth or abutment tooth model 10 to be scanned often has fine unevenness. In the case of non-contact scanning, a scanning light applied to the surface having the unevenness is irregularly reflected and returned to a light-receiving part, so that an error of about 0.002 mm to 0.01 mm is generally included. Therefore, even if the distance between two adjacent points of the multiple points 22 of the temporary finish line 23 is divided finer than the error, no effect can be obtained.

To restore the finish line 29 as accurately as possible, processing must be executed after division into pieces sufficiently smaller than the original tooth radius. A numerical value used as a reference is determined depending on the size of the abutment tooth or abutment tooth model 10 and the shape of the finish line 29. With regard to the maximum size, it is empirically known that when the interval between two adjacent points of the multiple points 22 is up to 1 mm, practically sufficient accuracy can be acquired when the radius has a largest value as in a molar tooth. If the distance between two adjacent points of the multiple points 22 is larger than 1 mm, a portion including small curves may be unreproducible.

The interval between the multiple points 22 of the temporary finish line 23 is often evenly assigned by the dental CAD and an operator generally accepts the result unless a problem occurs in reproduction of the shape. In this case, to acquire the temporary finish line 23 having high reproducibility at both a small radius portion and a large radius portion of the finish line formed on the tooth, the interval between the adjacent points is preferably within the range of 0.002 mm to 0.250 mm.

[Effect]

According to the method of estimating and restoring an abutment tooth form changed by scanning according to the present invention, the following effects can be produced.

In the method of estimating and restoring an abutment tooth form which is changed by scanning according to the present invention, the finish line of the abutment tooth or abutment tooth model is estimated and restored by deleting the scan data 21 of the edge portion and extending the temporary finish line 23. As a result, the abutment tooth form which is impaired by scanning can be estimated and restored. Consequently, an error can be reduced between the estimated and restored finish line 29 and the finish line of the actual abutment tooth or abutment tooth model, so that the estimation and restoration accuracy of the abutment tooth form can be improved.

As described above, according to the method of the present invention, the finish line originally possessed by the abutment tooth or abutment tooth model can accurately be estimated and restored, so that the peripheral form of the abutment tooth or abutment tooth model can highly accurately be reproduced.

Figure 13:
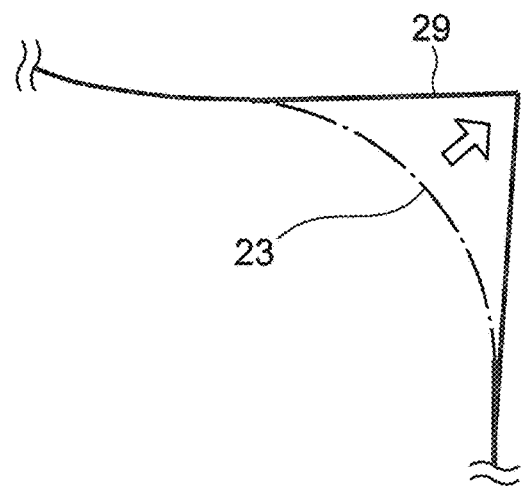
FIG. 13 is a schematic of a finish line which is estimated and restored by using an estimation and restoration method of an abutment tooth form according to the present invention.

FIG. 13 shows a finish line which is estimated and restored by using the estimation and restoration method according to the present invention. A dashed-dotted line of FIG. 13 indicates the temporary finish line 23 and a solid line indicates the estimated and restored finish line 29. As shown in FIG. 13, the scanned data which is scanned by a scanning device has the edge portion rounded as indicated by the temporary finish line 23. The estimated and restored finish line 29 has the edge portion which is made sharper than the temporary finish line 23 and has a shape fitting to the actual edge portion of the abutment tooth or abutment tooth model.

According to the estimation and restoration method of the present invention, the crown-side temporary finish line 23a is extended while maintaining the curvature, or a change ratio of the curvature, of the temporary finish line 23a near the crown-side cutting reference point 24. The root-side temporary finish line 23b is extended while maintaining the curvature, or a change ratio of the curvature, of the temporary finish line 23b near the root-side cutting reference point 25. In this way, by extending the temporary finish lines 23a and 23b based on the curvature, or a change ratio of the curvature, of the temporary finish lines 23a and 23b, the finish line 29 can be estimated and restored with further improved accuracy. Therefore, the error can be reduced between the estimated and restored finish line 29 and the finish line of the actual abutment tooth or abutment tooth model.

In the estimation and restoration method according to the present invention, the curvature, or a change ratio of the curvature, of the temporary finish line 23a near the crown-side cutting reference point 24 is preferably the curvature or a change ratio of the curvature which is calculated based on the temporary finish line 23a within a range of 0.1 mm from the crown-side cutting reference point 24 in the crown direction. The curvature, or a change ratio of the curvature, of the temporary finish line 23b near the root-side cutting reference point 25 is preferably the curvature or a change ratio of the curvature which is calculated based on the temporary finish line 23*b* within a range of 0.12 mm from the root-side cutting reference point in the root direction.

As a result of measurement of an error between the finish line 29 which is estimated and restored by performing the method according to the present invention within the numerical ranges described above and the finish line originally possessed by the abutment tooth model 10, it is confirmed that the error falls within a range of 0.002 mm to 0.040 mm in many cases. This is an error equal to or less than 0.03 mm to 0.04 mm, which is a reference of a visually confirmable gap between the abutment tooth and the prosthetic device. Therefore, by performing the method according to the present invention within the numerical ranges described above, the finish line of the actual abutment tooth can be reproduced with practically sufficient accuracy.

According to the estimation and restoration method of the present invention, since the finish line of the abutment tooth can be reproduced with sufficient accuracy, the necessity of adjustment of the finish line by a dental technician can be reduced.

In the example described in first embodiment, at step ST10, the scan data of the abutment tooth or abutment tooth model is acquired by the scanning device; however, the present invention is not limited thereto. For example, the scan data may be acquired by receiving data which is scanned by a dental technician or dentist via a network.

In the example described in the first embodiment, at step ST10, the temporary finish line 23 is determined annularly along the edge portion of the scan data 21 of the abutment tooth or abutment tooth model 10; however, the present invention is not limited thereto. For example, the temporary finish line 23 may be determined in a portion of the edge portion of the scan data 21 of the abutment tooth or abutment tooth model 10.

In the first embodiment, step ST40 may include performing either the method of extending the temporary finish line 23 based on the curvature or the method of extending the temporary finish line 23 based on a change ratio of the curvature or may include performing both of the methods.

If step ST40 includes performing both the method of extending the temporary finish line 23 based on the curvature and the method of extending the temporary finish line 23 based on a change ratio of the curvature, the intersection point 28 may be acquired at step ST51 by calculating a point at the outermost position from the tooth crown out of the intersection points which are calculated by the two methods.

For example, at step ST51, a first intersection point may be calculated by extending the crown-side temporary finish line 23*a* while maintaining the curvature of the temporary finish line 23*a* near the crown-side cutting reference point 24 and extending the root-side temporary finish line 23*b* while maintaining the curvature of the temporary finish line 23*b* near the root-side cutting reference point 25. Additionally, at step ST51, a second intersection point may be calculated by extending the crown-side temporary finish line 23*a* while maintaining a change ratio of the curvature of the temporary finish line 23*a* near the crown-side cutting reference point 24 and extending the root-side temporary finish line 23*b* while maintaining a change ratio of the curvature of the temporary finish line 23*b* near the root-side cutting reference point 25. Subsequently, the first intersection point and the second intersection point may be compared to calculate the point at the outermost position from the tooth crown as the intersection point 28 at which the extended crown-side temporary finish line 23*c* intersects with the root-side temporary finish line 23*d*.

With such a configuration, the finish line can more accurately be estimated and restored.

In the example described in the first embodiment, the surplus lines projecting outward beyond the intersection points 28 are trimmed off; however, the present invention is not limited thereto. For example, the extension may be stopped when the extended crown-side temporary finish line 23*c* and the extended root-side temporary finish line 23*d* are connected. As a result, no surplus line is generated and the need for trimming is eliminated.

In the example described in the first embodiment, the edge portion of the abutment tooth or abutment tooth model is entirely deleted before the finish line 29 is estimated and restored; however, the present invention is not limited thereto. For example, the finish line 29 of the edge portion may be estimated and restored in a portion of the abutment tooth or abutment tooth model.

For example, the estimation and restoration method of the present invention may include distinguishing in the temporary finish line 23 between a portion in which the finish line 29 is estimated and restored and a portion in which the finish line 29 is not estimated or restored, based on the curvature of the edge of the temporary finish line 23 in each of the cut sections. In this case, the temporary finish line 23 may directly be determined as the finish line 29 in the portion in which the finish line 29 is not estimated or restored. Alternatively, if the finish line 29 is already estimated and restored in the portion in which the finish line 29 is not estimated or restored, the finish line may be returned to the form of the temporary finish line 23.

With such a configuration, when a portion of the temporary finish line 23 is smooth rather than sharp, the finish line can be estimated and restored while the temporary finish line 23 is directly determined as the finish line in the sharp portion. Therefore, the finish line can be estimated and restored in the portion of the form impaired by scanning, while directly using the portion of the form not impaired by scanning. As a result, the abutment tooth form can highly accurately be reproduced and a data processing amount can be reduced. Whether the portion is smooth, for example, whether the finish line is estimated and restored, can be determined based on a threshold value of the curvature of the edge of the temporary finish line 23 in the cut section. The threshold value of the curvature can arbitrarily be determined by a user, for example.

In the first embodiment, the present invention may be implemented by a program for performing the method described above or a non-transitory computer readable storage medium in which a program for performing the method is recorded. For example, the non-transitory computer-readable storage medium may include the estimation and restoration method according to the present invention as a computer-readable instruction executable by a processor. The non-transitory computer-readable storage medium may include various types of volatile and nonvolatile storage mediums and may include, for example, a random access memory (RAM), a read only memory (ROM), a programmable read only memory (PROM), an electrically programmable read only memory (PROM), an electrically erasable read only memory (EPROM), a flash memory, some of other tangible data storage devices, and a combination of some of them.

Although described as the method of estimating and restoring an abutment tooth form which is changed by scanning in the first embodiment, the present invention can also be implemented as a system or a device which executes the method of estimating and restoring an abutment tooth form which is changed by scanning. For example, the system or the device of estimating and restoring an abutment tooth form which is changed by scanning includes a scan data acquiring part, a temporary finish line determining part, a cutting reference point detecting part, a crown-direction cutting line creating part, a root-direction cutting line creating part, a scan data deleting part, a temporary finish line extending part, an intersection point calculating part, and a finish line estimating/restoring part executing steps ST10 to ST50.

Second Embodiment

A second embodiment will be described in terms of a manufacturing system and a manufacturing method for manufacturing a prosthetic device by using the method of estimating and restoring an abutment tooth form which is changed by scanning of the first embodiment. In the second embodiment, differences from the first embodiment will mainly be described. In the second embodiment, the same or equivalent constituent elements as the first embodiment are denoted by the same reference numerals in the description. In the second embodiment, descriptions overlapping with the first embodiment will not be made.
[Manufacturing System of Prosthetic Device]

The manufacturing system of a prosthetic device according to the present invention will be described.

Figure 14:
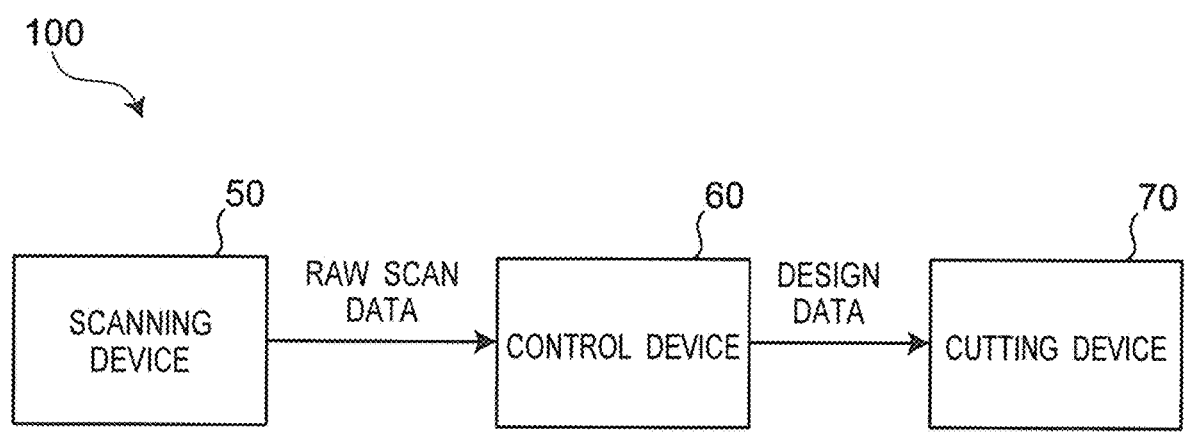
FIG. 14 is a block diagram of a schematic configuration of a prosthetic device manufacturing system according to the present invention.

FIG. 14 is a block diagram of a schematic configuration of a manufacturing system 100 for fabricating a prosthetic device according to the present invention. As shown in FIG. 14, the manufacturing system 100 includes a scanning device 50, a control device 60, and a cutting device 70.

The scanning device 50 is a device scanning the abutment tooth or abutment tooth model 10 to acquire raw scan data. The scanning device 50 is an intraoral scanner or a desktop scanner, for example.

The control device 60 is a device acquiring raw scan data from the scanning device 50 to create design data for designing the prosthetic device.

Figure 15:
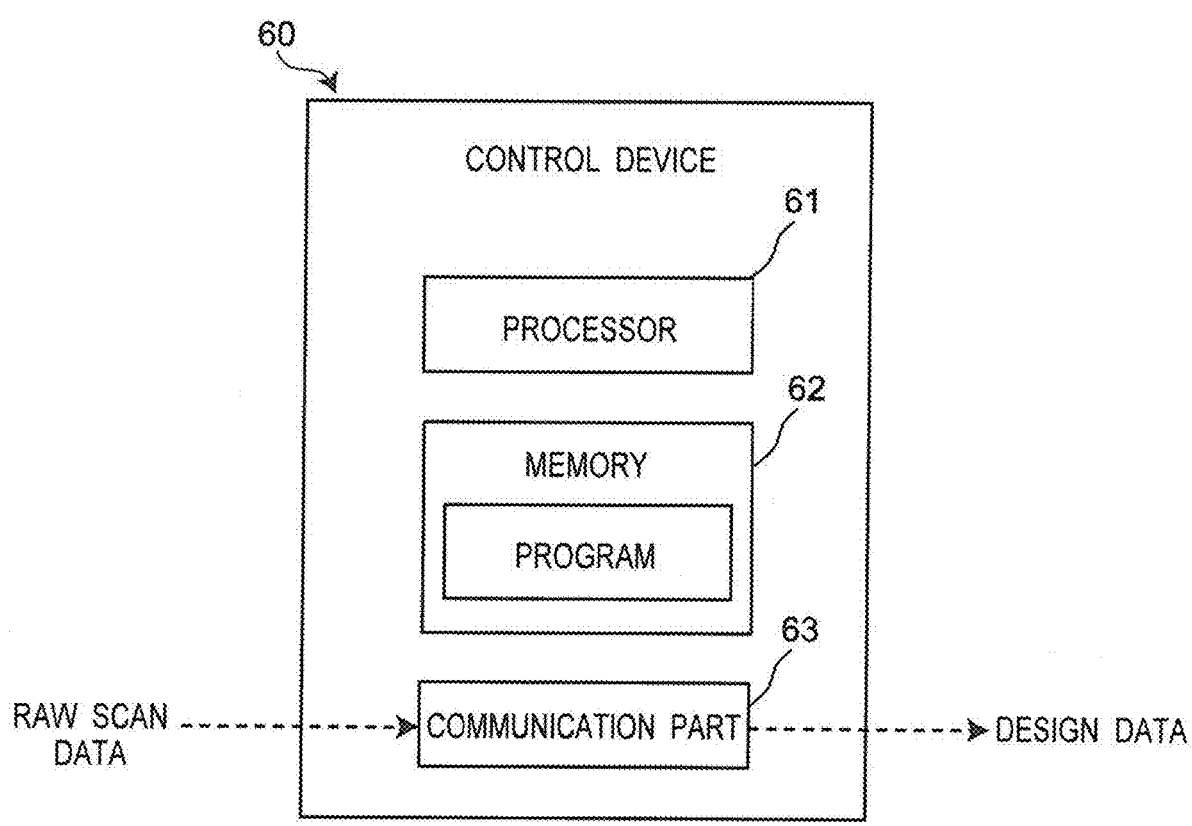
FIG. 15 is a block diagram of a schematic configuration of a control device.

FIG. 15 is a block diagram of a schematic configuration of the control device 60. As shown in FIG. 15, the control device 60 includes one or more processors 61, a memory 62, and a communication part 63.

The processor 61 is, for example, a central processing unit (CPU), a microprocessor, or other processing units capable of executing computer-executable instructions. The processor 61 is capable of executing instructions which are stored in the memory 62.

The memory 62 stores data of the control device 60. Examples of the memory 62 include computer storage mediums and include RAMs, ROMs, EEPROMs, flash memories, or other memory technologies, CD-ROMs, DVDs, or other optical disk storages, magnetic cassettes, magnetic tapes, magnetic disk storages, or other magnetic storage devices, or any mediums usable for storing desired information and capable of being accessed by the control device 60.

The memory 62 stores a program for performing the method of estimating and restoring an abutment tooth form of the first embodiment. The memory 62 stores a program for creating the design data of the prosthetic device 30 described later.

The communication part 63 receives raw scan data from the scanning device 50 via a network, for example. The communication part 63 transmits the design data of the prosthetic device to the cutting device 70 via a network, for example.

The cutting device 70 fabricates the prosthetic device 30 based on the design data which is created by the control device 60. In the second embodiment, a coping of zirconia is fabricated as the prosthetic device 30.
[Manufacturing Method of Prosthetic Device]

A manufacturing method of a prosthetic device which is performed by the manufacturing system 100 of a prosthetic device according to the present invention will be described.

Figure 16:
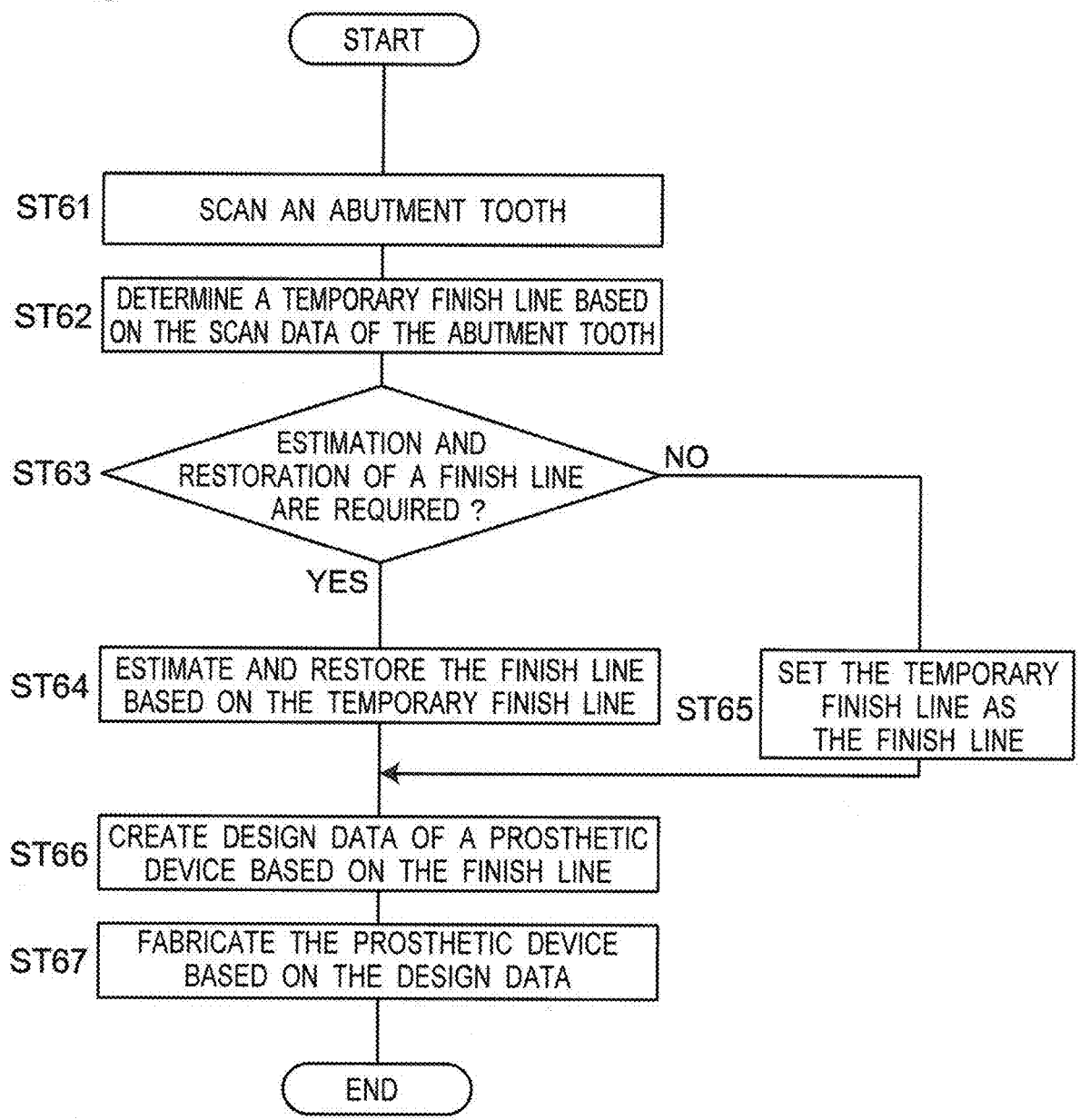
FIG. 16 is a flow chart of a manufacturing method of a prosthetic device according to the present invention.

FIG. 16 is a flowchart of the manufacturing method of a prosthetic device according to the present invention.

As shown in FIG. 16, at step ST61, the scanning device 50 scans the abutment tooth or abutment tooth model. As a result, the raw scan data of the abutment tooth or abutment tooth model is acquired. The acquired raw scan data is transmitted to the control device 60.

At step ST62, the control device 60 creates the scan data 21 composed of a parametric curve from the raw scan data and thereby determines the temporary finish line 23 having the multiple points 22 as an imaginary line of the edge portion of the abutment tooth or abutment tooth model.

At step ST63, the control device 60 determines whether the estimation and restoration of the finish line 29 are required. For example, whether the finish line 29 is estimated and restored is performed is determined based on a threshold value of the curvature of the edge of the temporary finish line 23. In this way, a portion requiring the estimation and restoration of the finish line 29 is detected in the edge portion of the scan data 21. The portion requiring the estimation and restoration of the finish line 29 corresponds to a portion which is impaired by scanning.

At step ST63, if it is determined that the estimation restoration of the finish line 29 is required, the process goes to step ST64. If it is determined at step ST63 that the estimation and restoration of the finish line 29 are not required, the process goes to step ST65.

At step ST64, the control device 60 estimates and restores the finish line 29 based on the temporary finish line 23. The estimation and restoration of the finish line 29 are the same as the estimation and restoration method of the first embodiment and therefore will not be described.

At step ST65, the control device 60 determines the temporary finish line 23 as the finish line 29. Therefore, at step ST65, the scan data 21 is directly applied to the finish line 29.

At step ST66, the control device 60 creates the design data of the prosthetic device 30 based on the finish line 29. Specifically, at step ST66, the finish line 29 which is estimated and restored at step ST64 and the finish line 29 determined at step ST65 are connected smoothly without inconsistency. Based on the finish line 29 acquired in this way, the peripheral form of the abutment tooth or abutment tooth model is reproduced. Forms other than the peripheral form are reproduced by the scan data 21. In this way, the control device 60 creates the design data of the prosthetic device 30. The created design data is transmitted to the cutting device 70.

At step ST67, the cutting device 70 fabricates the prosthetic device 30 based on the design data.
[Effects]

According to the manufacturing system and the manufacturing method of a prosthetic device according to the present invention, the following effects can be produced.

According to the manufacturing system 100 and the manufacturing method of the prosthetic device 30 according to the present invention, the finish line of the abutment tooth can be reproduced with sufficient accuracy, so that the prosthetic device with high fitting accuracy to the abutment tooth or abutment tooth model can be fabricated.

Figure 17:
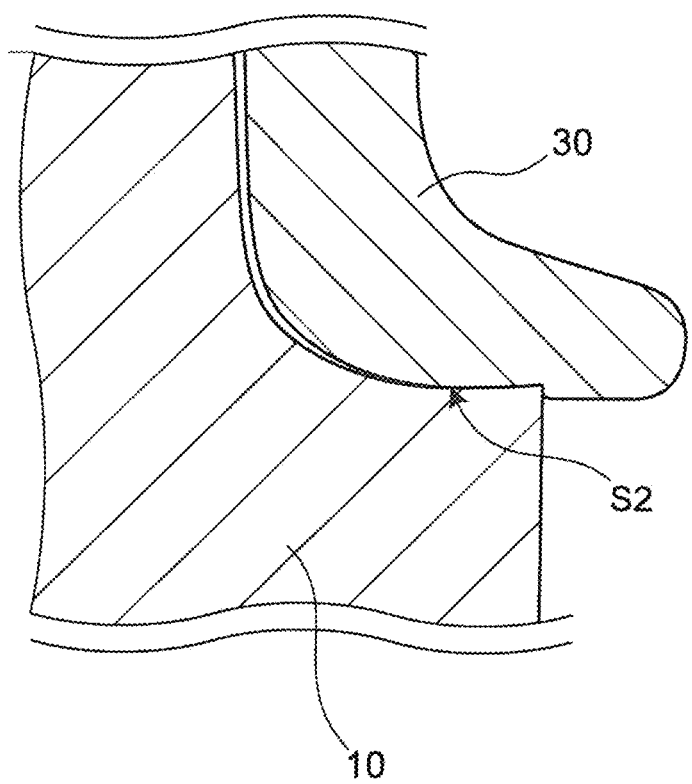
FIG. 17 is an enlarged schematic partial cross-sectional view of an edge portion when a prosthetic device fabricated by using the manufacturing method of the prosthetic device according to the present invention is attached to the abutment tooth model.

FIG. 17 is an enlarged schematic partial cross-sectional view of an edge portion when the prosthetic device 30 which is fabricated by using the manufacturing method of the prosthetic device 30 according to the present invention is attached to the abutment tooth model 10. As shown in FIG. 17, the prosthetic device 30 which is fabricated by using the manufacturing method of the prosthetic device 30 according to the present invention highly accurately fits to the edge portion of the abutment tooth model 10. Comparing FIGS. 10 and 17, it can be seen that a gap S2 between the abutment tooth model 10 and the prosthetic device 30 shown in FIG. 17 is made smaller than the gap S1 between the prosthetic device 30 which is fabricated based on the scan data 20 and the abutment tooth model 10 shown in FIG. 10.

As described above, according to the manufacturing system and manufacturing method of the present invention, the prosthetic device 30 with improved fitting accuracy to the abutment tooth or abutment tooth model can be fabricated.

According to the manufacturing system and the manufacturing method of the present invention, when the prosthetic device 30 is fabricated, adjustment of an inner crown portion which is performed by a dental technician can substantially be eliminated. Therefore, the time and effort spent by a dental technician for a crown adjustment work etc. become substantially unnecessary. Furthermore, since the work skill and experience which are required for performing these works are no longer necessary, even an inexperienced dental technician can easily fabricate the prosthetic device 30 with the same fitting accuracy as in the case of the work performed by an experienced dental technician.

The manufacturing system and the manufacturing method of the present invention can reduce the probabilities of occurrence of poor fitting of the prosthetic device 30, a tendency of the occlusal vertical dimension to become higher, a fracture during try-in, etc., so that a reduction in redundant treatment time and effort of dentists can be achieved.

Patients can acquire an effect of reducing physical and psychological burdens because of enhanced satisfaction due to improved fitting during wearing of the prosthetic device 30 designed and processed according to the present invention, a reduced possibility of revisit due to remanufacturing, decreases in the number of treatments and treatment time, as well as an effect of recovering the jaw oral cavity function as soon as possible.

In the example described in the second embodiment, the raw scan data of the abutment tooth or abutment tooth form is acquired by the scanning device 50, but the present invention is not limited thereto. In the manufacturing system 100 of the prosthetic device 30 according to the present invention, the scanning device 50 is not an essential constituent element, and step ST61 is not an essential constituent element in the manufacturing method. For example, the manufacturing system of the prosthetic device 30 according to the present invention may electronically receive raw scan data acquired by scanning performed by a dental technician or a dentist, or may receive an electronic recording medium having the raw scan data recorded thereon, so as to acquire the raw scan data.

In the example described in the second embodiment, the manufacturing system 100 includes the cutting device 70; however, the present invention is not limited thereto. For example, in the manufacturing system 100, design data created based on the estimated and restored finish line 29 may electronically be transmitted via a network to a dental technician or a dentist, or an electronic recording medium having design data recorded thereon may be sent to a dental technician or dentist. The prosthetic device 30 may be fabricated based on the design data received by the dental technician or the dentist in this way.

In the second embodiment, the control device 60 may include constituent elements executing steps of the manufacturing method. For example, the control device 60 may include a temporary finish line determining part, a finish line estimation restoration determining part, a finish line estimating/restoring part, and a design data creating part executing respective steps ST62 to ST66. The finish line estimating/restoring part may execute steps ST64 and ST65. Instead of the scanning device 50, the control device 60 may include a scan data acquiring part.

In the method and system of the first and second embodiments described above, the constituent elements may be added, reduced, divided, and integrated depending on an environment to which the present invention is applied.

Although the present invention has been described in some detail in terms of the embodiments, these contents of disclosure of the embodiments may obviously be changed in detail of configurations, and changes in combinations and orders of elements in the embodiments may be achieved without departing from the scope and the idea of the present invention.

INDUSTRIAL APPLICABILITY

The method of estimating and restoring an abutment tooth form which is changed by scanning according to the present invention enables estimation and restoration of the finish line of the abutment tooth or abutment tooth model impaired by scanning. Therefore, the present invention is useful for a device or a method for manufacturing a prosthetic device.

REFERENCE SIGNS LIST 10 abutment tooth model
20, 21 scan data
22 point
23 temporary finish line
23a crown-side temporary finish line
23b root-side temporary finish line
23c extended crown-side temporary finish line
23d extended root-side temporary finish line
24 crown-side cutting reference point
25 root-side cutting reference point
26 crown-direction cutting line
27 root-direction cutting line
28 intersection point
29 finish line
30 prosthetic device
50 scanning device
60 control device
61 processor
62 memory
63 communication part
70 cutting device
100 manufacturing system of prosthetic device

The invention claimed is:

1. A method of estimating and restoring a form near a finish line of an abutment tooth or abutment tooth model which is changed by scanning, the method comprising:

determining a temporary finish line having multiple points on scan data as an imaginary boundary line between a formed portion and an unformed portion of the abutment tooth or abutment tooth model by creating the scan data including three-dimensional data from raw scan data which is acquired by scanning the abutment tooth or abutment tooth model by a scanner;

deleting the scan data including the temporary finish line in an edge portion of the abutment tooth or abutment tooth model by creating a crown-direction cutting line and a root-direction cutting line, and deleting the scan data in an edge portion between the crown-direction cutting line and the root-direction cutting line;

extending, in a portion in which the scanned data is deleted, a crown-side temporary finish line and a root-side temporary finish line in directions supplementing the deleted portion of the scan data, respectively; and estimating and restoring the finish line which is formed on the outer side of the edge portion of the deleted scan data based on the extended crown-side temporary finish line and the extended root-side temporary finish line.

2. The method according to claim 1, wherein
the determining the temporary finish line includes annularly determining the temporary finish line along the edge portion of the scan data of the abutment tooth or abutment tooth model,
wherein the deleting the scan data further includes
detecting a crown-side cutting reference point and a root-side cutting reference point based on curvature of the temporary finish line on each of cut sections which is acquired by cutting the scan data of the abutment tooth or abutment tooth model at each of the multiple points of the temporary finish line on the scan data, along a plane including an arbitrary straight line extending from the root side to the crown side in a range surrounded by the temporary finish line, where the crown-side cutting reference point and the root-side cutting reference point serve as reference points for deleting the scan data in the edge portion,
creating the crown-direction cutting line by connecting the crown-side cutting reference points of the respective cut sections, and
creating the root-direction cutting line by connecting the root-side cutting reference points of the respective cut sections,
wherein the extending includes extending, in a portion in which the scanned data is deleted on each of the cut sections, the crown-side temporary finish line from the crown-side cutting reference point in a direction opposite to a crown direction and the root-side temporary finish line from the root-side cutting reference point in a direction opposite to a root direction, and
wherein the estimating and restoring the finish line includes
calculating an intersection point at which the extended crown-side temporary finish line intersects with the extended root-side temporary finish line in the portion in which the scanned data is deleted on each of the cut sections, and
estimating and restoring the finish line in the edge portion of the abutment tooth or abutment tooth model based on an intersection line which is created by connecting the intersection points calculated on the respective cut sections, the extended crown-side temporary finish line, and the extended root-side temporary finish line.

3. The method according to claim 2, wherein the detecting the crown-side cutting reference point and the root-side cutting reference point includes
detecting as the crown-side cutting reference point a first point at which the curvature of the temporary finish line in the crown direction becomes zero or a first point at which a radial direction of the curve thereof is reversed, and
detecting as the root-side cutting reference point a first point at which the curvature of the temporary finish line in the root direction becomes zero or a first point at which a radial direction of the curve thereof is reversed, on the cut section.

4. The method according to claim 2, wherein
the extending includes
extending the crown-side temporary finish line while maintaining the curvature, or a change ratio of the curvature, of the temporary finish line near the crown-side cutting reference point, and
extending the root-side temporary finish line while maintaining the curvature, or a change ratio of the curvature, of the temporary finish line near the root-side cutting reference point.

5. The method according to claim 4, wherein
the curvature, or a change ratio of the curvature, of the temporary finish line near the crown-side cutting reference point includes the curvature or a change ratio of the curvature calculated based on the temporary finish line within a range of 0.1 mm from the crown-side cutting reference point in the crown direction, and
wherein the curvature or a change ratio of the curvature calculated based on multiple points near the root-side cutting reference point includes the curvature or a change ratio of the curvature calculated based on the temporary finish line within a range of 0.12 mm from the root-side cutting reference point in the root direction.

6. The method according to claim 2, wherein
the calculating the intersection point includes
comparing a first intersection point and a second intersection point, where the first intersection point is calculated by extending the crown-side temporary finish line while maintaining the curvature of the temporary finish line near the crown-side cutting reference point and extending the root-side temporary finish line while maintaining the curvature of the temporary finish line near the root-side cutting reference point, and the second intersection point is calculated by extending the crown-side temporary finish line while maintaining a change ratio of the curvature of the temporary finish line near the crown-side cutting reference point and extending the root-side temporary finish line while maintaining a change ratio of the curvature of the temporary finish line near the root-side cutting reference point, and
calculating a point at an outermost position from a tooth crown out of the first intersection point and the second intersection point as the intersection point at which the extended crown-side temporary finish line intersects with the extended root-side temporary finish line.

7. The method according to claim 1, wherein a distance between the multiple adjacent points of the temporary finish line which is used for estimating and restoring the finish line is within a range of 0.002 mm to 1 mm.

8. The method according to claim 1, further comprising distinguishing in the temporary finish line between a portion in which the finish line is estimated and restored and a portion in which the finish line is not estimated or restored, based on the curvature of an edge of the temporary finish line in each of the cut sections, and determining the temporary finish line as the finish line in the portion in which the finish line is not estimated or restored.

9. A non-transitory computer-readable storage medium having stored thereon instructions executable by one or more processor to cause the one or more processor to execute functions comprising:

determining a temporary finish line having multiple points on scan data as an imaginary boundary line between a formed portion and an unformed portion of the abutment tooth or abutment tooth model by creating the scan data including three-dimensional data from raw scan data which is acquired by scanning the abutment tooth or abutment tooth model by a scanner;

deleting the scan data including the temporary finish line in an edge portion of the abutment tooth or abutment tooth model by creating a crown-direction cutting line and a root-direction cutting line, and deleting the scan data in an edge portion between the crown-direction cutting line and the root-direction cutting line;

extending, in a portion in which the scanned data is deleted, a crown-side temporary finish line and a root-side temporary finish line in directions supplementing the deleted portion of the scan data, respectively; and estimating and restoring the finish line which is formed on the outer side of the edge portion of the deleted scan data based on the extended crown-side temporary finish line and the extended root-side temporary finish line.

10. The non-transitory computer-readable storage medium according to claim 9, wherein the determining the temporary finish line includes annularly determining the temporary finish line along the edge portion of the scan data of the abutment tooth or abutment tooth model, wherein the deleting the scan data further includes detecting a crown-side cutting reference point and a root-side cutting reference point based on curvature of the temporary finish line on each of cut sections which is acquired by cutting the scan data of the abutment tooth or abutment tooth model at each of the multiple points of the temporary finish line on the scan data, along a plane including an arbitrary straight line extending from the root side to the crown side in a range surrounded by the temporary finish line, where the crown-side cutting reference point and the root-side cutting reference point serve as reference points for deleting the scan data in the edge portion, creating the crown-direction cutting line by connecting the crown-side cutting reference points of the respective cut sections, and creating the root-direction cutting line by connecting the root-side cutting reference points of the respective cut sections, wherein the extending includes extending, in a portion in which the scanned data is deleted on each of the cut sections, the crown-side temporary finish line from the crown-side cutting reference point in a direction opposite to a crown direction and the root-side temporary finish line from the root-side cutting reference point in a direction opposite to a root direction, and wherein the estimating and restoring the finish line includes calculating an intersection point at which the extended crown-side temporary finish line intersects with the extended root-side temporary finish line in the portion in which the scanned data is deleted on each of the cut sections, and estimating and restoring the finish line in the edge portion of the abutment tooth or abutment tooth model based on an intersection line which is created by connecting the intersection points which are calculated on the respective cut sections, the extended crown-side temporary finish line, and the extended root-side temporary finish line.

11. The non-transitory computer-readable storage medium according to claim 10, wherein the detecting the crown-side cutting reference point and the root-side cutting reference point includes detecting as the crown-side cutting reference point a first point at which the curvature of the temporary finish line in the crown direction becomes zero or a first point at which a radial direction of the curve thereof is reversed, and detecting as the root-side cutting reference point a first point at which the curvature of the temporary finish line in the root direction becomes zero or a first point at which a radial direction of the curve thereof is reversed, on the cut section.

12. The non-transitory computer-readable storage medium according to claim 10, wherein the extending includes extending the crown-side temporary finish line while maintaining the curvature, or a change ratio of the curvature, of the temporary finish line near the crown-side cutting reference point, and extending the root-side temporary finish line while maintaining the curvature, or a change ratio of the curvature, of the temporary finish line near the root-side cutting reference point.

13. The non-transitory computer-readable storage medium according to claim 12, wherein the curvature, or a change ratio of the curvature, of the temporary finish line near the crown-side cutting reference point includes the curvature or a change ratio of the curvature calculated based on the temporary finish line within a range of 0.1 mm from the crown-side cutting reference point in the crown direction, and wherein the curvature or a change ratio of the curvature calculated based on multiple points near the root-side cutting reference point includes the curvature or a change ratio of the curvature calculated based on the temporary finish line within a range of 0.12 mm from the root-side cutting reference point in the root direction.

14. The non-transitory computer-readable storage medium according to claim 10, wherein the calculating the intersection point includes comparing a first intersection point and a second intersection point, where the first intersection point is calculated by extending the crown-side temporary finish line while maintaining the curvature of the temporary finish line near the crown-side cutting reference point and extending the root-side temporary finish line while maintaining the curvature of the temporary finish line near the root-side cutting reference point, and the second intersection point is calculated by extending the crown-side temporary finish line while maintaining a change ratio of the curvature of the temporary finish line near the crown-side cutting reference point and extending the root-side temporary finish line while maintaining a change ratio of the curvature of the temporary finish line near the root-side cutting reference point, and calculating a point at an outermost position from a tooth crown out of the first intersection point and the second intersection point as the intersection point at which the extended crown-side temporary finish line intersects with the extended root-side temporary finish line.

15. The non-transitory computer-readable storage medium according to claim 9, wherein a distance between the multiple adjacent points of the temporary finish line which is used for estimating and restoring the finish line is within a range of 0.002 mm to 1 mm.

16. The non-transitory computer-readable storage medium according to claim 9, wherein the functions further comprising distinguishing in the temporary finish line between a portion in which the finish line is estimated and restored and a portion in which the finish line is not estimated or restored, based on the curvature of an edge of the temporary finish line in each of the cut sections, and determining the temporary finish line as the finish line in the portion in which the finish line is not estimated or restored.

17. A prosthetic device manufacturing method of estimating and restoring an abutment tooth form which is changed by scanning to fabricate a prosthetic device fitting to an abutment tooth or an abutment tooth model based on the estimated and restored abutment tooth form, the method comprising:

acquiring raw scan data of the abutment tooth or abutment tooth model;

determining a temporary finish line having multiple points as an imaginary boundary line between a formed portion and an unformed portion of the abutment tooth or abutment tooth model by creating scan data including of three-dimensional data from the raw scan data;

deleting the scan data including the temporary finish line in an edge portion of the abutment tooth or abutment tooth model by creating a crown-direction cutting line and a root-direction cutting line, and deleting the scan data in an edge portion between the crown-direction cutting line and the root-direction cutting line;

extending, in the portion in which the scanned data is deleted, a crown-side temporary finish line and a root-side temporary finish line in directions supplementing the deleted portion of the scan data, respectively;

estimating and restoring the finish line formed on the outer side of the edge portion of the deleted scan data based on the extended crown-side temporary finish line and the extended root-side temporary finish line; and fabricating the prosthetic device from design data created based on the finish line.

18. The prosthetic device manufacturing method according to claim 17, wherein the determining the temporary finish line includes annularly determining the temporary finish line along the edge portion of the scan data of the abutment tooth or abutment tooth model, wherein the deleting the scan data further includes detecting a crown-side cutting reference point and a root-side cutting reference point based on curvature of the temporary finish line on each of cut sections which is acquired by cutting the scan data of the abutment tooth or abutment tooth model at each of the multiple points of the temporary finish line on the scan data, along a plane including an arbitrary straight line extending from the root side to the crown side in a range surrounded by the temporary finish line, where the crown-side cutting reference point and the root-side cutting reference point serve as reference points for deleting the scan data in the edge portion creating the crown-direction cutting line by connecting the crown-side cutting reference points of the respective cut sections, and creating the root-direction cutting line by connecting the root-side cutting reference points of the respective cut sections, wherein the extending includes extending, in a portion in which the scanned data is deleted on each of the cut sections, the crown-side temporary finish line from the crown-side cutting reference point in a direction opposite to a crown direction the root-side temporary finish line from the root-side cutting reference point in a direction opposite to a root direction, and wherein the estimating and restoring the finish line includes calculating an intersection point at which the extended crown-side temporary finish line intersects with the extended root-side temporary finish line in the portion in which the scanned data is deleted on each of the cut sections, and estimating and restoring the finish line in the edge portion of the abutment tooth or abutment tooth model based on an intersection line which is created by connecting the intersection points which are calculated on the respective cut sections, the extended crown-side temporary finish line, and the extended root-side temporary finish line.

19. The prosthetic device manufacturing method according to claim 18, wherein the detecting the crown-side cutting reference point and the root-side cutting reference point includes detecting as the crown-side cutting reference point a first point at which the curvature of the temporary finish line in the crown direction becomes zero or a first point at which a radial direction of a curve is reversed, and detecting as the root-side cutting reference point a first point at which the curvature of the temporary finish line in the root direction becomes zero or a first point at which a radial direction of a curve is reversed, on the cut section.

20. The prosthetic device manufacturing method according to claim 18, wherein the extending includes extending the crown-side temporary finish line while maintaining the curvature, or a change ratio of the curvature, of the temporary finish line near the crown-side cutting reference point, and extending the root-side temporary finish line while maintaining the curvature, or a change ratio of the curvature, of the temporary finish line near the root-side cutting reference point.

* * * * *